(12) United States Patent
Bloch

(10) Patent No.: US 11,839,731 B2
(45) Date of Patent: Dec. 12, 2023

(54) CATHETER FOR DEEP NASAL INSERTION SPHENOPALATINE GANGLION ("SPG") TREATMENT

(71) Applicant: Sana Louis Bloch, West Hempstead, NY (US)

(72) Inventor: Sana Louis Bloch, West Hempstead, NY (US)

( * ) Notice: Subject to any disclaimer, the term of this patent is extended or adjusted under 35 U.S.C. 154(b) by 0 days.

(21) Appl. No.: 17/740,342

(22) Filed: May 9, 2022

(65) Prior Publication Data

US 2022/0409870 A1 Dec. 29, 2022

Related U.S. Application Data

(63) Continuation of application No. 17/144,128, filed on Jan. 7, 2021, now Pat. No. 11,324,934.

(60) Provisional application No. 63/025,270, filed on May 15, 2020, provisional application No. 62/957,900, filed on Jan. 7, 2020.

(51) Int. Cl.
*A61M 31/00* (2006.01)
*A61M 25/00* (2006.01)

(52) U.S. Cl.
CPC ......... *A61M 31/00* (2013.01); *A61M 25/0067* (2013.01); *A61M 2210/0618* (2013.01)

(58) Field of Classification Search
CPC ...... A61M 2210/0618; A61M 25/0074; A61M 31/00
See application file for complete search history.

(56) References Cited

U.S. PATENT DOCUMENTS

| | | | | |
|---|---|---|---|---|
| 8,388,600 B1 * | 3/2013 | Eldredge | ............... | A61M 31/00 604/514 |
| 2006/0287677 A1 * | 12/2006 | Shalev | ............... | A61N 1/36017 607/2 |
| 2011/0152838 A1 * | 6/2011 | Xia | ......................... | A61M 11/06 604/514 |
| 2017/0027645 A1 * | 2/2017 | Ben Oren | ............... | A61B 18/22 |
| 2018/0256867 A1 * | 9/2018 | Levin | ..................... | A61M 15/08 |

* cited by examiner

*Primary Examiner* — Deanna K Hall
(74) *Attorney, Agent, or Firm* — Law Offices Of Mitchell P. Novick

(57) ABSTRACT

This disclosure relates to procedures for administering a blockade of the sphenopalatine ganglion ("SPG"). Methods may include advancing a catheter through nostril at least 8 cm. Methods may include advancing the catheter through an inferior meatus. Methods may include causing the catheter to bend after contacting posterior wall of the nasal cavity. Methods may include advancing the catheter superiorly to a position posterior to the middle turbinate. Methods may include advancing the catheter superiorly to a position posterior to the superior turbinate. Methods may include advancing the catheter superiorly into a sphenoethmoid recess. Methods may include bringing a distal tip of the catheter in contact with the SPG. Methods may include ejecting an anesthetic from a distal tip of the catheter and bathing the SPG to administer a blockade of the SPG.

8 Claims, 17 Drawing Sheets

CATHETER FOR DEEP NASAL INSERTION SPHENOPALATINE GANGLION ("SPG") TREATMENT

CROSS REFERENCE TO RELATED APPLICATIONS

This application is a continuation of U.S. Non-Provisional Utility patent application Ser. No. 17/144,128, filed on Jan. 7, 2021, which claims priority to U.S. Provisional Application No. 62/957,900, filed on Jan. 7, 2020 and U.S. Provisional Application No. 63/025,270, filed on May 15, 2020, all of which are hereby incorporated by reference herein in their entireties.

PATIENT DATA APPENDIX

This application includes patient data as an appendix. The appendix includes two (2) files (submitted via EFS-Web). The appendix (all two files) is hereby incorporated by reference herein in its entirety.

The table below lists the two files included in the appendix:

| File No. | File Name | Date Created | File Size (kilobytes) |
| --- | --- | --- | --- |
| 1 | Appendix_A.pdf | Jan. 7, 2021 | 792 |
| 2 | Appendix_B.pdf | Jan. 7, 2021 | 809 |

FIELD OF INVENTION

This disclosure relates to procedures for administering a blockade of the sphenopalatine ganglion.

BACKGROUND

Cephalalgia (e.g., headaches) impose a substantial burden on patients in terms of diminished daily functioning, quality of life, and financial loss. Pain severity and duration correlates with reduced measures of daily functioning, and overall health status. The sphenopalatine ganglion ("SPG," also known as the pterygopalatine ganglion) has been implicated in a variety of cephalalgias.

The SPG is the largest group of neurons outside the cranial cavity and lies in the pterygopalatine fossa ("PPF"). The SPG has been implicated in treating head and face pain for over a century. Because of its anatomical connections and role in the trigemino-autonomic reflex, it is widely accepted that disruption, or blockade of neural signals generated by the SPG can modulate the output of the autonomic nerve fibers involved in headaches.

Stimulation of the SPG can be used to treat ischemic stroke. However, the currently available approaches for inserting an electrical stimulator at or near the SPG are invasive (involving penetration of the mucosa on the lateral nasal wall) or expensive (requiring fluoroscopic guidance). Conventionally, blockade of the SPG is accomplished by attempting to administer local anesthetics to areas near the SPG. An SPG block using local anesthesia is non-invasive and relatively inexpensive.

The SPG is housed in the PPF which is located inside the nasal cavity near the lateral insertion of the posterior middle turbinate. The middle turbinate is open at its anterior and posterior ends. The PPF is approximately 1-cm wide and approximately 2-cm high. The PPF is bordered anteriorly by the posterior wall of the maxillary sinus, posteriorly by the medial plate of the pterygoid process, medially by the perpendicular plate of the palatine bone, and superiorly by the sphenoid sinus. Laterally, the pterygopalatine fossa communicates with the infratemporal fossa.

Because of the SPG's anatomical position, the SPG is hard to access from outside the body and block with a local anesthetic solution. The PPF is deep inside the nasal cavity. The SPG is tucked within the PPF and there is no easy, direct, "line-of-sight" access to the SPG through the nostrils or other body orifices. Unfortunately, many current methods and apparatus for administering a SPG block are cumbersome, invasive, and expensive.

The PPF is close to vital and delicate structures emanating from the mid brain, such as delicate orbital branches, which pass directly to the apex of the orbit and eventually the lacrimal gland. Therefore, although under fluoroscopic guidance a syringe may be used to inject medicant directly to the SPG, practitioners will typically not attempt this procedure due to danger of an erroneous needle placement.

Access to the SPG can be gained via a small area of mucosa just posterior and superior to a posterior end of the middle turbinate on a lateral wall of the nasal cavity. At this aspect, there is no bony boundary to the SPG. Various intranasal devices and associated techniques have been developed for administering a SPG blockade intranasally. Currently, available intranasal devices include the SphenoCath® catheters and the Tx360® nasal applicator.

The SphenoCath® includes a flexible outer sheath and an inner, extendible catheter with a curved tip. To administer a SPG block using the SphenoCath®, a patient is placed in a supine position with cervical spine extension. The outer sheath is inserted into a nostril and advanced though an anterior portion of the nasal cavity using tactile judgment for proper placement.

The practitioner attempts to navigate the outer sheath of the SphenoCath® from the anterior nasal passage to a position superior to a middle nasal turbinate and anterior to the SPG. After the outer sheath is successfully advanced through the anterior portion of the nasal cavity and positioned superior to the middle turbinate, the outer sheath is retracted, and a distal tip of the inner catheter is exposed. An anesthetic agent is then released from the distal tip of the inner catheter. Commonly, 1 to 2 mL of 2% lidocaine is used as the anesthetic agent when administering a SPG block using the SphenoCath®.

Following release of the anesthetic agent, the SphenoCath® is removed from the nasal cavity and the procedure is repeated on the opposite side if needed. The patient is maintained in a supine position for 8-10 minutes during the procedure.

However, the aforementioned and approved method for using the SphenoCath® is difficult for the practitioner and uncomfortable for the patient. Advancing the outer sheath through the anterior portion of the nasal cavity requires navigating the SphenoCath® through the anterior area of the nasal cavity which is rich in vascular and neuronal structures. The practitioner must skillfully navigate the SphenoCath® to avoid contact with these sensitive structures. Because contact with these sensitive structures is inevitable, even by the most skilled practitioner, patients experience discomfort during conventional procedures using the SphenoCath®.

Furthermore, because the SPG is anatomically positioned closer to a posterior wall of the nasal cavity, all the anesthetic agent released by the SphenoCath® does not reach the SPG, reducing efficacy of the treatment. Because of the varied anatomy of patients, sometimes a practitioner can only advance the SphenoCath® about 3-4 centimeters ("cm") into the nasal cavity. When attempting to access the SPG by inserting a catheter though the anterior nasal cavity, practitioners may find it difficult or impossible to insert the catheter even 5 cm into the nostril. Advancing the catheter only 5 cm or less keeps a distal tip of the catheter relatively far from the SPG. However, the patient may not be able to tolerate any further discomfort and the practitioner typically will release the anesthetic agent at that point and hope at least some of the anesthetic agent will be applied to the SPG.

In contrast to the methods associated with the SphenoCath®, a SPG blockade performed using the Tx360® device is administered with the patient seated and upright. The Tx360® device is advanced parallel to the floor of the nasal cavity (e.g., hard palate). The Tx360® is advanced until a distal catheter tip is positioned inferior to the SPG.

The Tx360® includes a straight but flexible catheter which is capable navigating curvatures along the floor of the nasal cavity. The flexibility of the catheter allows a distal tip of the catheter to extend to a position that is posterior to the inferior turbinate. However, the distal tip of the flexible does not extend superior to the inferior turbinate and does not reach a posterior end of the middle turbinate.

After the flexible catheter is fully extended past the inferior turbinate, medicament is then released through the distal catheter tip. The medicament is delivered by the Tx360® laterally, superiorly, and anteriorly towards the SPG. The Tx360® is designed to release 1 cc or less of an anesthetic mixture. The lower dosage is due to the assumption that the Tx360® may position the distal catheter tip closer to the SPG and therefore less medicament is required to effectively blockade the SPG.

The Tx360® cannot be used to release medicament from regions of the nasal cavity that are superior to the inferior or middle turbinates. The flexible catheter of the Tx360® is too short to extend at least 8 cm into the nasal cavity. The flexible catheter associated with the Tx360® is less than 1 mm in diameter. The flexible catheter of the Tx360® is too flimsy and would not be able to bend and advance superiorly from its insertion position inferior to the inferior turbinate.

Although, methods for delivering of medicament to the SPG using the Tx360® show some efficacy, the improvement in headache pain was not significant compared to placebo groups. See, e.g., Matthew S. Robbins, M D, et al., The Sphenopalatine Ganglion: Anatomy, Pathophysiology, and Therapeutic Targeting in Headache, Headache 2016; 56:240-258, American Headache Society. Evidence suggests a potential for more acute benefits with repetitive SPG blocks over time. However, this is cumbersome for practitioners and ensuring patient compliance may be challenging.

It would be desirable to provide improved methods for administering an SPG block that is more effective than other methods. It would also be desirable to provide methods for administering an SPG block that are minimally abrasive and well tolerated by patients. Accordingly, it would be desirable to provide DEEP NASAL INSERTION SPHENOPALATINE GANGLION ("SPG") TREATMENT.

BRIEF DESCRIPTION OF THE DRAWINGS

The objects and advantages of the disclosure will be apparent upon consideration of the following detailed description, taken in conjunction with the accompanying drawings, in which like reference characters refer to like parts throughout, and in which.

DETAILED DESCRIPTION

Figure 1:
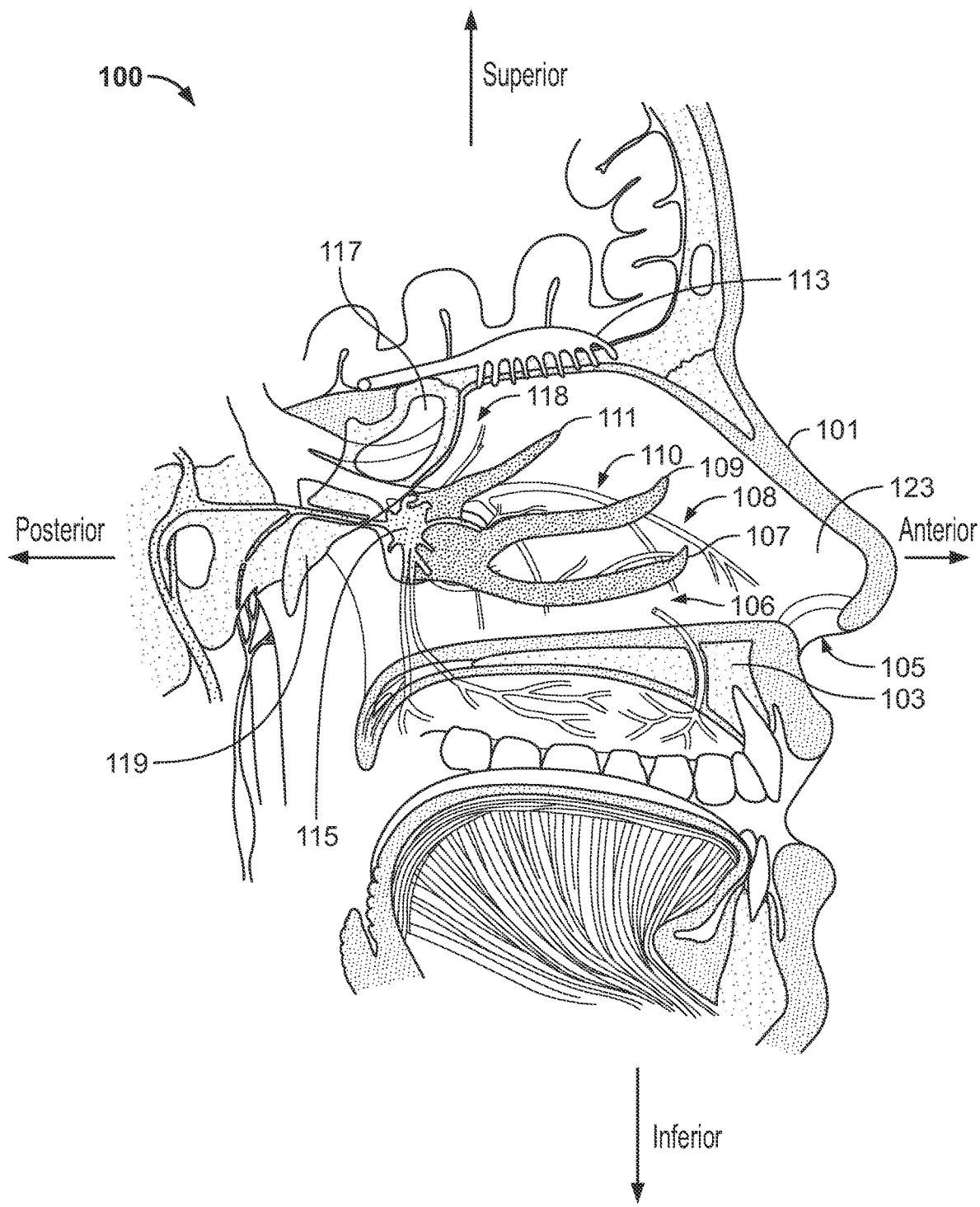
FIG. 1 shows an illustrative anatomical features of a human nasal cavity.

Methods for delivering medicament to a sphenopalatine ganglion ("SPG") are provided. Data for 250 patients demonstrating efficacy of the methods for administering a SPG block in accordance with this disclosure is shown in Appendix A (pre-procedure status) and Appendix B (post-procedure status).

Methods may be used to treat acute migraine headaches, chronic migraine headaches, post-traumatic headaches, tension headaches, vascular headaches, trigeminal neuralgia, depression, posttraumatic syndrome disorder ("PTSD"), schizophrenia, obsession compulsion disorder ("OCD"), cerebrovascular accidents ("CVA"), any type of epilepsy, or any other suitable diagnoses or conditions.

The methods may be used for adult patients, geriatric patients, pediatric patients, neonatal patients, or any other suitable patients. The methods may be performed in both nostrils of a patient.

Methods may include advancing a catheter at least 8 centimeters ("cm") into a nostril of a patient. The catheter may be advanced through the inferior meatus. In practice, when inserting the catheter though the inferior meatus, a distal tip of the catheter has been 100% successfully advanced at least 8 cm past the nostril for 600 patients and 1,200 nostrils. "Distal," relative to "proximal," generally means the leading end of an apparatus that is inserted, or is to be inserted, in the body. Proximal general means the end of the apparatus that is held by a practitioner when inserting the apparatus into the body.

The catheter may be a flexible catheter. A flexible catheter may include a catheter that bends in response to contact with tissue or other anatomical structures within the nasal cavity. A flexible catheter may be sufficiently rigid to advance past tissue or other anatomical structures that may obstruct or divert a path of the catheter.

For example, a flexible catheter inserted through a nostril in a posterior direction will bend in a superior direction in response to contacting a torus tubarius or other structures at or near a posterior wall of the nasal cavity. Further advancement of the flexible catheter though the nostril in the posterior direction will cause the catheter to advance further in a superior direction.

A flexible catheter may be constructed from Tecothane®, an aromatic polyurethane available from Lubrizol Advanced Materials, Inc. of Cleveland, Ohio. An illustrative flexible catheter may have a hardness that ranges from 20 A-80 A on the Shore hardness scale.

Methods may include positioning a distal tip of the catheter posterior and superior to a middle turbinate of the patient. Methods may include releasing the medicament from the distal tip of the catheter. Releasing medicament may include ejecting medicament from the distal tip. A proximal end of the catheter may be affixed to a syringe filled with the medicament. Actuating a plunger of the syringe may move the medicament out of a syringe barrel, through the catheter and out of the distal tip of the catheter.

In a preferred embodiment, a single lumen catheter is sufficient for performing SPG blockade procedures described herein and a device (e.g., SphenoCath® catheter part number DT1001GP-3, available from Dolor Technologies LLC, Clearfield, Utah) that includes an outer sheath and inner catheter are not needed. A single lumen catheter may be manufactured more economically and with less moving parts. The single lumen device may be manufactured with a flexibility that is comparable to flexibility of a SphenoCath® catheter when an inner catheter of the SphenoCath® is recessing within an outer sheath of the SphenoCath®.

In some embodiments, an inner catheter may be slidable within an outer sheath. In such embodiments, the outer sheath may be more rigid than the inner catheter. In embodiments that include an outer sheath and an inner catheter, the inner catheter may not be rigid enough to advance past tissue or other anatomical structures that may obstruct or divert a path of the catheter. The outer sheath may bend in response to contact with tissue or other anatomical structures within the nasal cavity and be sufficiently rigid to advance past tissue or other anatomical structures that may obstruct or divert a path of the outer sheath.

Methods may include positioning a distal tip of the inner catheter within the outer sheath. Methods may include inserting a distal tip of the outer sheath into a nostril of a patient. Methods may include inserting a distal tip of the outer sheath at least 8 cm into a nostril of a patient. Methods may include retracting the outer sheath. Retracting the outer sheath may expose the distal tip of the inner catheter.

The distal tip of the inner catheter may be biased to have a pre-defined curvature. When the distal tip of the inner catheter is covered by the outer sheath, the outer sheath may overcome the bias of the inner catheter's distal tip and align the distal tip of the inner catheter with the outer sheath. Retracting the outer sheath may expose the distal tip of the inner catheter and allow the distal tip of the inner catheter to revert to its biased curved state. When in the biased, curved state, the distal tip of the inner catheter may be oriented in a direction that deviates from a longitudinal axis of the outer sheath.

Releasing medicament may include ejecting the medicament from the distal catheter tip toward the SPG. Releasing medicament may include flooding the SPG with 3 cc of medicament, rather than spraying 1.5 cc or less of medicament. Releasing the medicament may include ejecting the medicament from the distal catheter tip along a trajectory that extends from the distal catheter tip inferiorly (e.g., downward) towards the SPG. For example, methods may position the distal catheter tip superior to the SPG. The distal catheter tip may then apply medicament to the SPG in an inferior direction.

Releasing the medicament may include ejecting the medicament from the distal catheter tip along a trajectory that begins at the distal catheter tip and extends superiorly within the nasal cavity towards the SPG. For example, the distal catheter tip may be positioned inferior to the SPG. The distal catheter tip may then apply medicament to the SPG in a superior direction.

Methods may include adjusting a proximal end of the catheter such that the distal catheter tip is within 4 millimeters ("mm") of a PPF of the patient. Methods may include adjusting a proximal end of the catheter such that the distal catheter tip is within 4 mm of a SPG of the patient. Methods may include, contacting the SPG with the distal catheter tip. The distal catheter tip may be positioned such that it contacts the SPG and medicament released from the distal catheter tip is applied directly to the SPG.

Methods may include advancing a catheter parallel to a superior surface of a hard palate of the patient. Methods may include advancing the catheter within the nasal cavity between the superior surface of the hard palate and an inferior turbinate of the patient. Methods may include advancing the catheter through an inferior meatus of the patient.

Methods may include advancing the distal catheter tip to a position that is superior and posterior to a middle turbinate of the patient. For example, the catheter may be advanced within the nasal cavity until the distal catheter tip contacts a posterior wall of the nasal cavity. Further advancement of the catheter through the inferior meatus may cause the catheter to bend.

Advancing the catheter through the inferior meatus may bring the catheter into contact a torus tubarius and/or the posterior nasal cavity. The torus tubarius is a mucosal protrusion in the lateral wall of the nasopharynx marking the pharyngeal end of the cartilaginous part of the eustachian tube. The torus tubarius is anterior to the salpingopharyngeal fold and is formed by the underlying pharyngeal end of the cartilaginous portion of the Eustachian tube. The opening of the Eustachian tube is anterior and inferior to the torus tobarius.

Contact with the torus tubarius while advancing the catheter through the inferior meatus may deflect the catheter in a superior direction, toward the posterior end of the middle turbinate. Contact with the torus tubarius may cause the catheter to bend at least 10 degrees. Contact with the torus tubarius may cause the catheter to bend at least 30 degrees.

After contact with the posterior wall of the nasal cavity, the path of least resistance for the catheter may be upwards in a superior direction. After deflecting superiorly, the distal catheter tip may ascend posteriorly to the inferior turbinate in a superior direction. The distal catheter tip may ascend superiorly past a posterior end of the middle turbinate.

Methods may include advancing the catheter through a nostril into the nasal cavity until the distal catheter tip contacts the body of the sphenoid bone. Contact with the sphenoid bone may direct the distal catheter tip in anterior or inferior direction. Contact with the sphenoid bone may bend the catheter. Contact with the sphenoid bone may bend the catheter at least 45 degrees. Contact with the sphenoid bone may bend the catheter at least 90 degrees.

Methods may include continuing to advance the catheter into the nostril such that a distal catheter tip is positioned posterior and superior to a superior turbinate of the patient. Methods may include advancing the catheter through a nostril into the nasal cavity until the distal catheter tip ascends into a sphenoethmoid recess. The sphenoethmoidal recess is a small space in the nasal cavity into which the sphenoidal sinus and posterior ethmoid sinus open. The sphenoethmoidal recess is posterior and superior to the superior turbinate. The sphenoethmoidal recess drains the posterior ethmoid air cells and sphenoid sinuses into the superior meatus of the nasal cavity.

Methods may include positioning the catheter inside a nasal cavity of the patient such that a first length of the catheter bends 90 degrees relative to a second length of the catheter. The bend may demarcate the first and second lengths of the catheter. The bend may be positioned posterior to the inferior turbinate. The bend may be positioned posterior to the middle turbinate. The bend may be positioned superior to the inferior turbinate. The bend may be positioned superior to the middle turbinate. The bend may be positioned touching the torus tobarius.

The second length of the catheter may extend superiorly relative to the first length. The first length may be substantially parallel to a hard palate of the patient. The first length may be oriented at an angle of at least 10 degrees relative to a superior surface of a hard palate of the patient. The first length may be positioned in an inferior meatus of the patient. The first length may extend over a torus tobarius of the patient.

The second length may extend superiorly from the first length. The second length may position the distal catheter tip superior to the inferior turbinate. The second length may position the distal catheter tip superior to the middle turbinate. The second length may position the distal catheter tip in a sphenoethmoid recess of the patient. Methods may include positioning the distal catheter tip in a sphenoethmoid recess of the patient before releasing the medicament from the distal catheter tip.

Methods may include advancing the distal catheter tip a distance of at least 8 cm into the nostril of the patient. Methods may include advancing the distal catheter tip a distance of at least 9 cm into the nostril. Methods may include advancing the distal catheter tip a distance of at least 10 cm into the nostril. Methods may include advancing the distal catheter tip a distance of at least 11 cm into the nostril. Methods may include advancing the distal catheter tip a distance of at least 12 cm into the nostril. Methods may include advancing the distal catheter tip to a position that is at least 1 cm from the SPG. Methods may include advancing the distal catheter tip to a position that is at least 4 millimeters ("mm") from the SPG.

Methods may include releasing medicament from the distal catheter tip when the distal catheter tip is positioned within 1 cm of the SPG. Releasing the medicament when the distal catheter tip is within 1 cm of the SPG may provide a blockade of the SPG that is more effective than prior-art methods.

Methods for delivering medicament to a sphenopalatine ganglion ("SPG") of a patient are provided. Methods may include introducing a catheter into a nostril of the patient. The catheter may be advanced through an inferior meatus of the patient. Advancing the catheter through the inferior meatus may cause the catheter to bend at a first position inside a nasal cavity. The first position may be posterior to the inferior turbinate.

Methods may include advancing the catheter superiorly to a second position in the nasal cavity. The second position may be posterior to a middle turbinate of the patient. The second position may be superior to the SPG of the patient. The second position may be in the same traverse plane as the SPG of the patient.

Apparatus may not include an outer sheath and inner catheter. Apparatus for performing methods herein may include a single lumen catheter that is at least 8 cm in length. Methods embodiments that utilize a single lumen catheter may not require recessing an outer sheath. Using methods disclosed herein, the distal tip of the single lumen catheter may be positioned superior to or touching the SPG. Medicament may be ejected from the distal tip of the single lumen catheter which bathes the SPG and achieves an effective SPG blockade. The single lumen catheter may be manufactured with a flexibility that is comparable to flexibility of a SphenoCath® catheter when an inner catheter of the SphenoCath® is recessing within an outer sheath of the SphenoCath®.

Some embodiments may utilize apparatus that does include an outer sheath and inner catheter. Methods may include recessing the outer sheath. Recessing the outer sheath may expose the distal catheter tip. The outer sheath may be recessed at least 1 cm. Methods may include releasing medicament from the distal catheter tip. Methods may include releasing at least 3 cc of medicament from the distal catheter tip.

Methods may include advancing the distal catheter tip to the second position within 15 seconds of introducing the catheter into the nostril. Methods may include advancing the distal catheter tip to the second position within 30 seconds of introducing the catheter into the nostril. Methods may include releasing the medicament when the distal catheter tip is in the second position. Methods may include positioning the distal catheter tip superior and posterior to the SPG before releasing the medicament. Methods may include positioning the distal catheter tip in the same traverse plane as the SPG before releasing the medicament. Methods may include positioning the distal catheter tip in a sphenoethmoid recess of the patient before releasing the medicament.

Methods may include advancing the distal catheter tip at least 8 centimeters ("cm") past the nostril of the patient. Methods may include advancing the distal catheter tip at least 8 cm past the nostril within 15 seconds of introducing the catheter into the nostril. Methods may include advancing the distal catheter tip at least 10 cm past the nostril of the patient. Methods may include advancing the distal catheter tip at least 12 cm past the nostril of the patient.

Methods may include rotating the catheter so that the distal catheter tip is pointing in an anterior direction (e.g., toward a bridge of the patient's nose). Methods may include advancing the distal catheter tip through the inferior meatus while biasing the catheter in a superior direction. Biasing the catheter in the superior direction may cause the catheter to bend when the catheter contacts a posterior wall of the nasal cavity. Biasing the catheter in the superior direction may cause the catheter to bend at the first position and the distal catheter tip continuing to advance in the superior direction to a position that is posterior to the inferior turbinate.

Methods may include advancing the distal catheter tip through the inferior meatus and bringing the catheter into contact with a posterior wall of the nasal cavity. Methods may include bringing the catheter into contact with a torus tubarius. Methods may include inserting a catheter at least 8 cm into a nasal cavity and bypassing an anterior region of the nasal cavity that is rich in vascular structures. Bypassing the anterior region of the nasal cavity may reduce patient discomfort when performing a SPG blockade procedure.

A method of intranasal treatment is provided. The methods may include inserting a catheter into a nostril of a patient. The method may include positioning a distal tip of the catheter within a nasal cavity posterior to a medial turbinate of the patient. The methods may include releasing at least 3 cubic centimeters ("cc") of medicament from the distal tip of the catheter in each nostril when the distal tip is positioned posterior to the medial turbinate.

The method may include advancing the distal catheter tip through an inferior meatus and at least 8 centimeters ("cm") past the nostril. The method may include recessing an outer sheath at least 1 cm out of the nostril before releasing medicament from the distal catheter tip. Recessing the outer sheath may expose distal catheter tip. Inserting the distal catheter tip into the nostril and through the inferior meatus while covered with the outer sheath may allow the distal catheter tip to be advanced within the nasal cavity to target location with respect to the SPG. Recessing the outer sheath when the distal catheter tip is at the target location may allow the distal catheter tip to bend in a pre-biased direction. The bending of the distal catheter tip in the pre-biased direction may bring the distal catheter tip closer to or in contact with the SPG.

The method may include positioning the distal catheter tip in a sphenoethmoid recess of the patient. The method may include positioning the distal catheter tip in a posterior region of the sphenoethmoid recess. The method may include positioning the distal catheter tip in a sphenoethmoid recess of the patient within 15 seconds of introducing the catheter into the nostril.

The method may include positioning the distal catheter tip in a sphenoethmoid recess before releasing the medicament. The method may include positioning the distal catheter tip in the nasal cavity such that when the outer sheath is recessed, the distal catheter tip contacts the SPG. The pre-biased direction of the distal catheter tip may bring the distal catheter tip into contact with the SPG.

The nostril may be a first nostril. The method may include inserting the distal catheter tip into a second nostril of the patient. The method may include positioning the distal catheter tip within the nasal cavity posterior to the medial turbinate and superior to inferior turbinate. The method may include causing the catheter to bend at least 90 degrees before releasing the at least 3 cc of medicament.

The method may include releasing at least 3 cc of medicament from the distal catheter tip when the distal catheter tip is positioned posterior to the medial turbinate and superior to inferior turbinate. The method may include releasing at least 3 cc of medicament from the distal catheter tip when the distal catheter tip is positioned posterior and superior to the medial turbinate.

A neurologist or other qualified practitioner may perform the aforementioned methods for administering a SPG blockade at an ambulatory surgical unit. The patient may be introduced to an intake nurse who takes a history of the patient's headache symptoms. Such history may include headache frequency and intensity on a scale of 1-10. Such history may include medical and allergy history. Such history may include medications taken presently and in the past for headaches.

The patient's vital signs are taken, and temperature strips are placed on each zygomatic arch of the patient. The patient is placed in a supine position on an examination bed and the patient's head is lowered 20° below the plane of the bed. Each of the patient nostril's is anesthetized with 0.5 cc of 2% lidocaine delivered by a conical atomizer. Approximately five minutes later, a 2% lidocaine gel is applied to each nostril via a cotton swab.

A flexible catheter, such as the SphenoCath® is dipped in 2% lidocaine gel. The flexible catheter is then inserted into the nostril parallel to a superior surface of the patient's hard palate. The catheter passes below (inferior) to the inferior turbinate. The catheter may pass through an inferior meatus. The catheter may be advanced parallel to a superior surface of the hard palate.

The catheter may be advanced until contacting a posterior wall of the nasal cavity. The catheter may then be further advanced, causing the catheter to deflect upwards (superiorly), bending 90 degrees and advancing the distal catheter tip to a position behind (posterior) the middle turbinate. The distal catheter tip is inserted at least 8 cm past the nostril. In some embodiments, the distal catheter tip may extend superiorly to the middle turbinate. In some embodiments, the distal catheter tip may extend into a posterior portion of the sphenoethmoid recess.

After being advanced at least 8 cm into the nostril and through an inferior meatus, an outer sheath may be recessed about 1 cm. The catheter may be rotated so that a distal catheter tip is pointing anteriorly towards a bridge of the nose. The catheter may be rotated so that a distal catheter tip is pointing toward a lateral wall of the nasal cavity.

After exposing and rotating the distal catheter tip, 3 cc of 2% lidocaine or other local anesthetic is rapidly pushed out of the distal catheter tip. The 3 cc of medicament floods the area in the vicinity of the SPG and all the surrounding nerves. The process is then repeating in the other nostril. A total of 6 cc of medicament is applied, 3 cc in each nostril. The patient is then asked to drink water through a straw which immediately washes away any excess medicament.

In over 600 cases (1,200 nostrils) this methods of administering a SPG blockade has not been associated with aspiration or choking. After 10 minutes, the patient sits upright and is given juice to drink. After 45 minutes, the patient is discharged home. Only 3% of patients may experience temporary vertigo which may lass up to 6 hours and requiring emergency room admission for hydration and IV Zofran.

The methods described herein were applied to a cohort of 148 patients. Each of these patients met inclusion criteria based on The International Classification of Headache Disorders 3rd edition (ICD-3) criteria for migraine, probable migraine, and chronic migraine. The mean age of patients was 49 years old. Patients received treatment for their headaches using the methods for administering a SPG block by inserting a flexible catheter parallel to a superior surface of the hard palate. A distal tip of the catheter was advanced at least 8 cm into the nasal cavity in accordance with this disclosure.

One hundred and eight patients (72.9%) reported improvement after the SPG block using methods disclosed herein. Of these 108 patients, 21 patients reported no headaches after 3 months, 13 patients reported no headaches after 6 months, and 30 patients reported complete resolution of headaches. Additionally, after receiving the SPG block in accordance with methods disclosed herein, patients experienced statistically significant reductions (p<0.0001) in both headache pain and frequency.

Illustrative scrubbed data for patients that have been administered a SPG block using the methods disclosed herein is included in Appendix A (pre-procedure status) and Appendix B (post-procedure status).

Methods described herein may include directing medicament through a catheter to the sphenoethmoid recess. The catheter may include an inner tube and an outer sheath. The catheter may include a handle. The handle may include a hub. The tube may include a distal tip that may be extendable from and retractable into the sheath at the end of the catheter that is opposite the handle. The distal tip may have a curve that does not deform the outer sheath when the distal tip is retracted. The methods may include placing the distal tip in the sphenoethmoid recess. The methods may include manipulating the catheter in the patient's anatomy to place the distal tip in the sphenoethmoid recess.

Methods for treating the sphenopalatine ganglion ("SPG") are described herein. The methods may be performed in the order described. The methods may be performed in an order different from the order described. The methods may include each of the steps listed below. The methods may include some, but not all, of the steps listed below.

The methods may include positioning a patient such that the patient is lying down on a flat bed. The methods may include injecting an analgesic, such as lidocaine, in each of the patients' nostrils using a syringe. The methods may include injecting 0.5 ccs of lidocaine in each nostril, or any other suitable amount.

The methods may include positioning the patient in the supine position, the body's frontal plane horizontal. The patient's head may be placed at an offset angle below the frontal plane. The offset angle may be 5, 8, 10, 12, 14, 16, 18, 20, 22, 24, 26, 28 or 30 degrees, including any intermediate values, and any range or subrange that may be defined by the enumerated angles.

The methods may include pushing the patient's chin up towards the ceiling. The methods may include immersing a cotton swab in an analgesic, such as 2% lidocaine gel, or any other suitable analgesic, and swabbing each of the patient's nostrils with the cotton swab. For an adult, the cotton swab may be inserted approximately 3 centimeters into each nostril.

The methods may include advancing a catheter into a first nostril. The catheter may be a flexible catheter. The catheter may be sufficiently flexible to deform in the anatomy such that it can be advanced to the sphenoethmoid recess as described below. The catheter may be 2 cm, 2.5 cm, 3 cm, 3.5 cm, 4 cm, 4.5 cm, 5 cm, 5.5 cm, 6 cm, 6.5 cm, 7 cm, 7.5 cm, 7.9 cm, 8 cm, 8.1 cm, 8.5 cm, 9 cm, 9.5 cm, 10 cm, including any intermediate values, and any range or subrange that may be defined by the enumerated lengths, or any other suitable length. The catheter may be part of a spool. The catheter may be delivered robotically.

The catheter may be a catheter that is semi-rigid. The catheter may define a curved shape that defines the path described below between the nostril and the sphenoethmoid recess.

The catheter may be advanced into the nostril when the patient is lying on the bed with the patient's head at an angle below the plane of the bed. The methods may include positioning the patient's chin so that it points towards the ceiling prior before advancing the catheter.

The catheter may have one or more of the properties, such as length, wall thickness, inner diameter, outer diameter, and material of an 8-cm SphenoCath® catheter, part number DT1001GP-3, provided by Dolor Technologies LLC, Clearfield, Utah, or any other suitable properties.

Prior to advancing the catheter into the first nostril, the catheter may be immersed in an analgesic, such as 2% lidocaine gel. The methods may include advancing the catheter into the first nostril. At the nostril, the catheter may initially be positioned with tip at the nostril, and shaft parallel the body's sagittal plane. The shaft may be canted at an insertion angle that increases away from the body's transverse plane (as imagined intersecting the nostril and perpendicular to the longitudinal axis of the head—that is, irrespective of the offset angle), toward the forehead. The insertion angle may be 0, 1, 2, 3, 4, 5, 6, 7, 8, 9, 10 degrees, including any intermediate values, and any range or subrange that may be defined by the enumerated angles. For reference the sagittal profile of the bridge of the nose may correspond to an angle of 120-140 degrees.

The methods may include continuing to advance the catheter through the nasal cavity. The catheter may be sufficiently flexible to then curve upwards in response to the patient's anatomy. The upward direction may be the path of least resistance for the catheter. The catheter may have pre-shaped curvature to curve upwards.

The methods may include advancing the catheter such that the distal tip of the catheter passes behind the medial (or middle) meatus, towards the position of the sphenoethmoid recess, and then continuing to advance the catheter until it is positioned in the sphenoethmoid recess. At insertion into the nostril, the distal tip may be retracted. The distal tip first may be extended to navigate the catheter to the medial meatus. The tip first may be extended to navigate the catheter into the sphenoethmoid recess. The distal tip first may be extended to position the tip, within the sphenoethmoid recess, adjacent the sphenopalatine ganglion. The distal tip first may be extended to position the tip, within the sphenoethmoid recess, in a position abutting the sphenopalatine ganglion. A practitioner may rotate one (relative to the other) or both (together) of the tube and the catheter, with the distal tip extended, to navigate to the medial meatus. The practitioner may rotate one (relative to the other) or both (together) of the tube and the catheter, with the tip extended, to navigate to the sphenoethmoid recess.

The methods may include advancing the catheter such that the distal tip of the catheter passes behind the medial (or middle) turbinate, towards the position of the sphenoethmoid recess, and then continuing to advance the catheter until it is positioned in the sphenoethmoid recess.

At insertion into the nostril, the distal tip may be retracted. The distal tip first may be extended to navigate the catheter behind the medial turbinate. The distal tip first may be extended to navigate the catheter to a location behind the medial turbinate. The distal tip first may be extended to navigate the catheter into the sphenoethmoid recess. The distal tip first may be extended to position the tip, within the sphenoethmoid recess, adjacent the sphenopalatine ganglion. The distal tip first may be extended to position the distal tip, within the sphenoethmoid recess, in a position abutting the sphenopalatine ganglion. A practitioner may rotate one (relative to the other) or both (together) of the tube and the catheter, with the distal tip extended, to navigate to a location behind the medial turbinate. The practitioner may rotate one (relative to the other) or both (together) of the tube and the catheter, with the distal tip extended, to navigate to the sphenoethmoid recess.

The practitioner may rotate one (relative to the other) or both (together) of the tube and the catheter, with the distal tip extended, to position the distal tip, within the sphenoethmoid recess, in a position abutting the sphenopalatine ganglion. The practitioner may rotate one (relative to the other) or both (together) of the tube and the catheter, with the distal tip extended, to position the distal tip, within the sphenoethmoid recess, in a position adjacent the sphenopalatine ganglion.

For an adult, the methods may include advancing the catheter through the first nostril at least 8-cm to position the distal tip of the catheter in the sphenoethmoid recess. The methods may include advancing the catheter through the first nostril to position the distal tip of the catheter in the sphenoethmoid recess. The advancing may include advancing the distal tip 8 cm past the nostril. An 8 cm advancement may correspond to placement of the distal tip in the sphenoethmoid recess.

For a patient having a different sized anatomy, and for whom a distance between the nostril and the sphenoethmoid recess, along the path taken by the catheter described above, is "X" cm, methods may involve advancing the catheter "X" cm through the nostrils, using the methods described herein, to position the distal tip of the catheter in the sphenoethmoid recess.

The methods may include, after a length of the catheter has been advanced through the nose such that the distal tip of the catheter is positioned in the sphenoethmoid recess, recessing the catheter and ejecting an analgesic as lidocaine, ketamine, cocaine, procaine, Novocain, Marcaine, gabapentoids, or any suitable analgesic or opioid. The ejected analgesic or opioid may bathe the SPG.

The methods may include ejecting 1.5 ccs of 2% lidocaine. The methods may include ejecting 3 ccs of 2% lidocaine. The methods may include ejecting any other suitable amount of cc's of lidocaine, such as 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10 cc's, including any intermediate values, and any range or subrange that may be defined by the enumerated amounts, or any other suitable amount.

The methods may include removing the catheter. The methods may include giving the patient a drink after the catheter is removed to flush out residual analgesic from the patient's throat and to remove from the patient the sensation that he is unable to drink. The patient may be given a drink 15 seconds after the catheter is removed, or after 10 seconds, 20 seconds, or any other suitable time interval.

The catheter may then be re-immersed in an analgesic, such as 2% lidocaine gel, and inserted into the second nostril as described above in connection with the first nostril. Upon completion of the procedure described above, the patient may be permitted to sit up after 5 minutes. After 45 minutes, the patient may leave the physician's office. The methods may be repeated for a patient after 4 months, 5 months, 6 months, or any other suitable time interval.

Typical methods for treating a patient suffering from the effects of a stroke involve positioning a stimulator into the pterygopalatine canal in the sphenopalatine ganglion. An image-guided navigation system is used, such as the ischemic stroke system guide view from BrainsGate Limited, Caesarea, Israel. The typical methods include an injection done under local anesthesia into the canal by a puncture into the mucosa of the upper palate and then insertion of the neurostimulator through this puncture hole. When the stimulator is positioned in the appropriate pterygopalatine canal adjacent the sphenopalatine ganglion, the stimulate is stimulated. The stimulate measures 23 mm long and 2 mm in diameter. Such known methods are described in public literature, such as in the article entitled "An injectable implant to stimulate the sphenopalatine ganglion for treatment of acute ischaemic stroke up to 24 h from onset (ImpACT-24B): an international, randomized, double-blind, sham-controlled, pivotal trial," by Natan M. Bronstein et al., published at www.thelancet.com, volume 394, pages 219-229, on Jul. 28, 2019.

These typical methods involve highly invasive steps. It would be desirable, therefore, to provide improved method and apparatus for positioning a stimulator at the SPG to treat stroke patients and any other suitable patients.

The apparatus may include a catheter including a stimulator. The stimulator may be a neurostimulator. The stimulator may include a neurostimulator electrode. The stimulate may be mounted on a distal tip of the catheter. Electrical wires for powering the stimulate may pass through the catheter and out a proximal end of the catheter. The electrical wires may be connected to a power source after exiting the proximal end of the catheter.

The stimulator may be positioned at a distal tip of the catheter. The stimulator may be positioned on a distal tip of the catheter. The stimulator may extend through the catheter and an end of the stimulator configured for stimulation may be positioned on, or coupled to, a distal tip of the catheter, such as the distal tip of the catheter. The catheter may have one or more of the properties, such as length, wall thickness, inner diameter, outer diameter, and material of an 8-cm SphenoCath® catheter, part number DT1001GP-3, for sale by Dolor Technologies LLC, Clearfield, Utah, or any other suitable properties. The catheter may include an electrical transmitter-control unit at a proximal end of the catheter for controlling the stimulator.

The distal tip, when retracted, may be positioned in a bore extending through the catheter. The bore may have a diameter of 3 mm, 2.9 mm, 2.8 mm, 2.7 mm, 3.1 mm, 3.2 mm, 3.3 mm, or any other suitable diameter. The stimulator may have a maximum diameter of 2 mm, 2.1 mm, 2.2 mm, 2.3 mm, 2.4 mm, 2.5 mm, 2.6 mm, 2.7 mm, or any other suitable maximum diameter.

The delivery catheter and/or the stimulator may have a length of 23 mm, 22 mm, 21 mm or any other suitable length. The delivery catheter and/or the stimulator may have a length of at least 8 cm, 8.1 cm, 8.2 cm, 8.5 cm, 9 cm, or any other suitable length.

The methods may include advancing the catheter through the nostril and positioning the catheter at the SPG in accordance with the methods described herein. The distal tip may be positioned in the bore during some or all of the advancing. The distal tip may be positioned in the bore during some or all of the positioning. The positioning may include extending the distal tip to position the stimulator at the SPG. When the stimulator is positioned at the SPG, the stimulator may be stimulated.

The catheter may remain in the nostril for a period of time while the stimulation is occurring. The stimulation level, and the duration of the stimulation, may be selected based on patient needs. When stimulation is completed, the catheter may be removed from the nostril.

The methods may include advancing the stimulator through the nose and positioning an end of the stimulator at the SPG in accordance with the methods described herein. The stimulator may be advanced with the delivery catheter. The stimulator may be advanced without a delivery catheter. The methods may not include bathing the SPG with a medicament. The methods may include bathing the SPG with a medicament such as a medicament described herein.

Apparatus for administering an SPG blockade is provided. Apparatus may include a sheath hub and an outer sheath. The outer sheath may be coupled to and extend from a distal portion of the sheath hub. Apparatus may include a catheter hub slidably connected to the sheath hub. Apparatus may include an inner catheter configured to slide within the outer sheath. Some apparatus embodiments may not include the inner catheter or catheter hub. In such embodiments, the outer sheath may function as the conduit for delivering medicament to the SPG. In embodiments that do not include the inner catheter, the outer sheath may include one or more properties (e.g., length, wall thickness, inner diameter, outer diameter, and material) of the outer sheath of a SphenoCath® catheter, part number DT1001GP-3, provided by Dolor Technologies LLC, Clearfield, Utah.

An end of the inner catheter may be biased to have an intrinsic curvature. For embodiments that include the inner catheter, the inner catheter may be slidably coupled to and extendable from a distal portion of the catheter hub. The intrinsic curvature may be straightened when the biased end of the inner catheter is positioned within the outer sheath. When the outer sheath is retracted, the inner catheter may extend from a distal tip of the outer sheath. When the inner catheter extends from the distal tip of the sheath, the intrinsic curvature of the inner catheter may point a distal tip of the inner catheter away from the outer sheath.

Apparatus and methods in accordance with this disclosure will now be described in connection with the figures, which form a part hereof. The figures show illustrative features of apparatus and method steps in accordance with the principles of this disclosure. It is to be understood that other embodiments may be utilized, and that structural, functional and procedural modifications may be made without departing from the scope and spirit of the present disclosure.

Method steps may be performed in an order other than the order shown and/or described herein. Method embodiments may omit steps shown and/or described in connection with illustrative methods. Method embodiments may include steps that are neither shown nor described in connection with illustrative methods. Illustrative method steps may be combined. For example, an illustrative method may include steps shown in connection with any other illustrative method described herein.

Apparatus may omit features shown and/or described in connection with illustrative apparatus. Apparatus embodiments may include features that are neither shown nor described in connection with illustrative apparatus. Features of illustrative apparatus may be combined. For example, an illustrative apparatus embodiment may include features shown or described in connection with any other illustrative apparatus and/or method embodiment.

FIG. 1 shows a sagittal view 100 of the inside of nasal cavity 123. A superior surface of hard palate 103 forms part of an inferior boundary of nasal cavity 123. Nose bridge 101 forms part of an anterior boundary of nasal cavity 123. Olfactory bulb 113 is positioned on a superior boundary of nasal cavity 123. A posterior boundary of nasal cavity includes sphenoid bone 119. Sphenoid bone 119 houses sphenoidal sinus 117.

At a posterior/inferior corner of the nasal cavity, the torus tubarius (not shown) extends from a lateral wall of nasal cavity 123 and surrounds the pharyngeal opening to the auditory tube. The salpingopharyngeal folds (not shown) descend inferiorly from the torus tubarius between the pharyngeal recess (not shown) and soft palate (not shown).

Nostril 105 provides access to an interior of nasal cavity 123. Inferior turbinate 107 is located in nasal cavity 123. Inferior meatus 106 is defined by space within nasal cavity 123 between inferior turbinate 107 and hard palate 103. Middle turbinate 109 is located in nasal cavity 123. Middle meatus 108 is defined by space within nasal cavity 123 between inferior turbinate 107 and middle turbinate 109. Superior turbinate 111 is located in nasal cavity 123. Superior meatus 110 is defined by space within nasal cavity 123 between middle turbinate 109 and superior turbinate 111. Sphenoethemoid recess 118 is superior to superior meatus 111, posterior to superior turbinate 110 and anterior to sphenoid bone 119.

SPG 115 is housed under a thin (1-2 mm) layer of mucosa and housed in the PPF (not shown). The SPG 115 is typically located between posterior ends of superior and middle turbinates 111 and 109. SPG 115 plays a unique role in headache disorders. SPG 115 is a key structure responsible for the expression of cranial autonomic symptoms, most seen in cephalalgias. Blockade of SPG 115 is thought to relieve headaches or other cephalalgias by targeting these specific neurological pathways central to headache pathophysiology. For example, SPG 115 includes a direct connection to the maxillary branch of the trigeminal nerve which may explain why blockade of SPG 115 may contribute to its efficacy in relieving migraines.

As opposed to blockade of SPG 115, stimulation of SPG 115 has been shown to activate cerebral vasodilatation and increase cerebral blood flow. Activation of SPG 115 may result in the release of acetylcholine, vasoactive intestinal peptide and nitric oxide in dural blood vessels. This may increase plasma protein extravasation with resultant neurogenic inflammation and activation of trigeminal nociceptors contributing to pain and triggering headache. However, timely increasing cerebral blood flow through stimulation of SPG 115 may relieve potentially debilitating symptoms associated with acute ischaemic strokes.

Animal studies have shown that stimulation of SPG 115 leads to arterial vasodilatation and a profound increase in ipsilateral cerebral blood flow, as well as augmentation of tissue perfusion. Stimulation of SPG 115 may preserve penumbra and reduce cerebral infarct volume, increase neuronal survival, preserve the blood-brain barrier leading to reduced cerebral oedema, and improve neurological outcomes for acute ischaemic stroke patients.

Figure 2A:
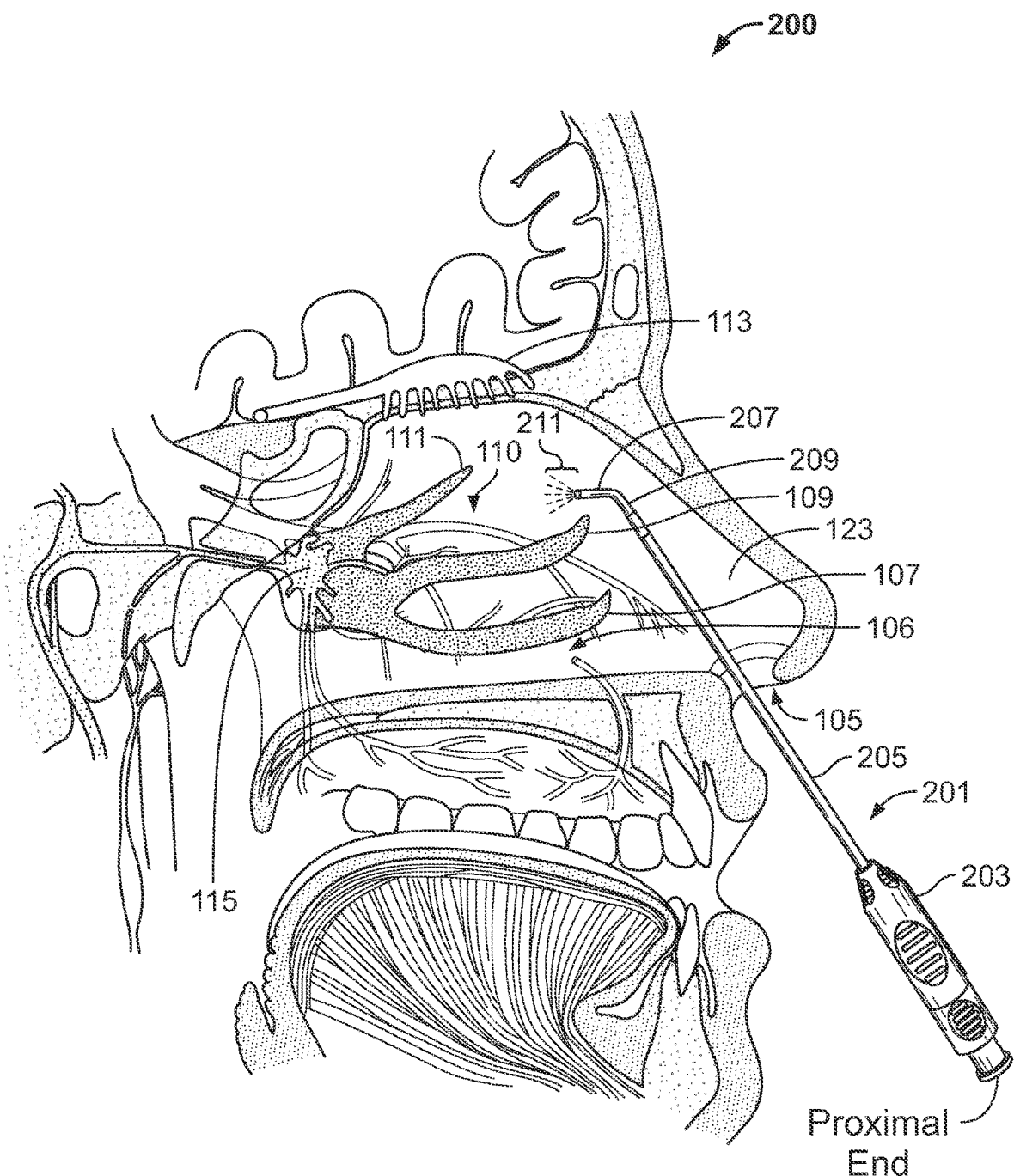
FIG. 2A shows an illustrative prior-art method of administering an SPG block.

FIG. 2A shows an illustrative prior-art method 200 for blockading SPG 115. Method 200 includes inserting catheter 201 into nostril 105. Catheter 201 may be a SphenoCath®. Methods 200 includes advancing outer sheath 205 of catheter 201 into nasal cavity 123 in a generally superior direction, passing anterior to inferior, middle and superior turbinates 107, 109 and 111. Typically, outer sheath 205 is inserted 5-6 cm into nasal cavity 123. After outer sheath 205 is positioned inside nasal cavity 123, outer sheath 205 is retracted out of nostril 105, exposing distal tip 207. Distal tip 207 is biased with pre-determined bend 209. When distal tip 207 is covered by outer sheath 205, outer sheath 205 aligns distal tip 207 with a length of outer sheath 205.

After outer sheath 205 is retracted and distal tip 207 exposed, catheter 201 is rotated using handle 203. Rotation of handle 203 points distal tip 207 towards an expected position of SPG 115. The practitioner then releases medicament 211 from distal tip 207. To achieve an effective block of SPG 115, medicament 211 must travel from distal tip 207 through middle meatus 110 to reach SPG 115.

However, method 200 does not allow distal tip 207 to be positioned directly on SPG 115. Using method 200, some of medicament 211 may be absorbed by superior turbinate 111, reducing efficacy of the procedure. Using method 200, medicament 211 must travel through middle meatus 110, reducing efficacy of the procedure. Turbinates 107, 109 and 111 are thick and moist tissue structures, designed to warm and humidify air drawn into nasal cavity 123. The distance medicament 211 must travel causes medicament 211 to be absorbed and diverted by other structures within nasal cavity 123, and reducing an amount of medicament 211, if any, applied to SPG 115.

Additional, method 200 requires insertion of outer sheath 205 through an anterior portion of nasal cavity 123, which is typically uncomfortable for a patient. Inserting outer sheath 205 anterior to turbinates 107, 109 and 111 requires traversing a region of nasal cavity 123 that is rich in vascular and neuronal structures. Contact with these structures may be painful for the patient. For example, during insertion, outer sheath 205 may contact delicate nerve endings of olfactory bulb 113.

Additionally, the structures in the anterior portion of nasal cavity 123 may obstruct the passage of outer sheath 205. In practice, outer sheath 205 may only be inserted 3-4 cm beyond nostril 205. Inserting outer sheath 205 only 3-4 cm may position distal tip 207 relatively far from SPG 115. The practitioner may release medicament 211 from distal tip 207 and hope that at least some of medicament 211 reaches SPG 114 ("spray and pray").

Figure 2B:
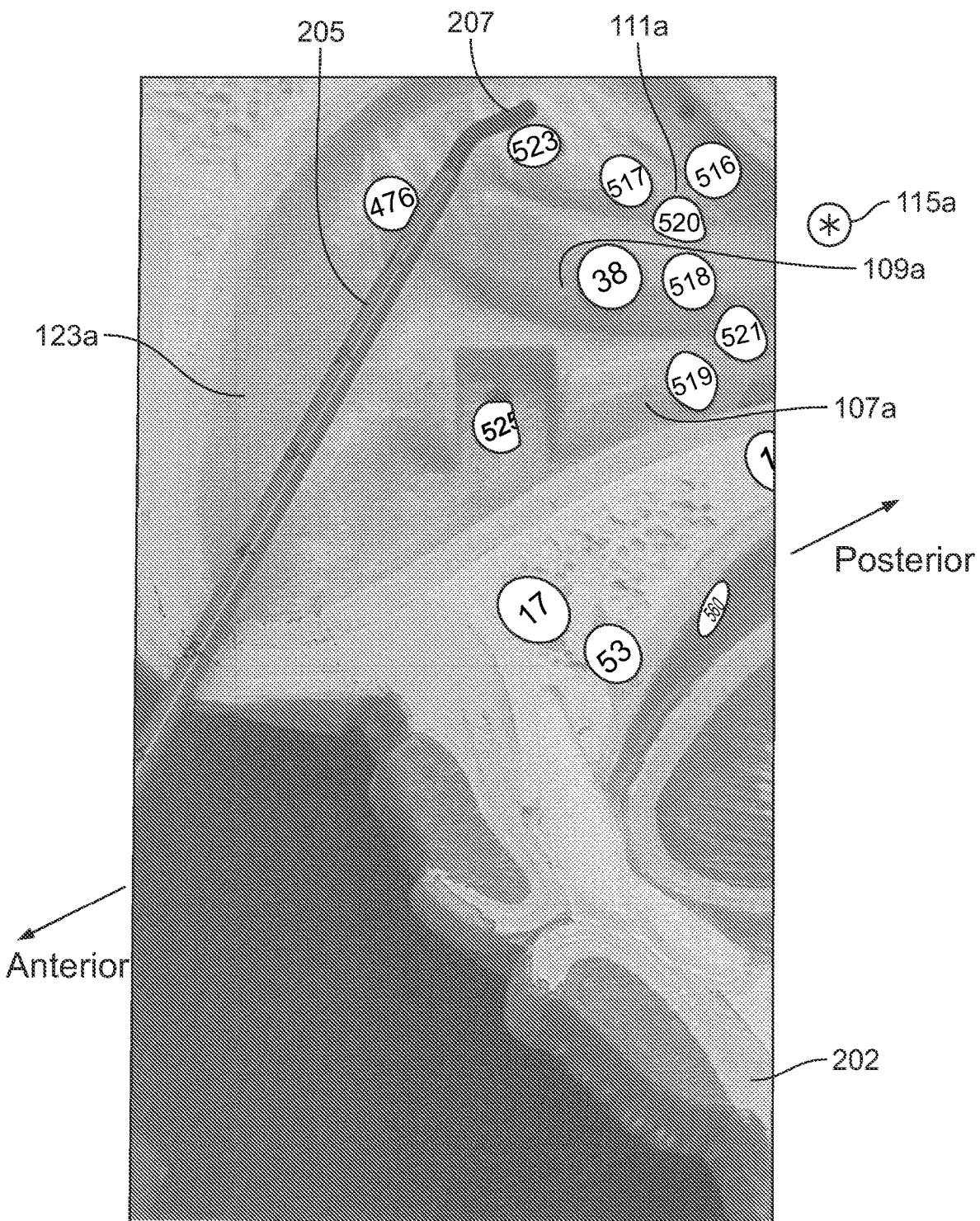
FIG. 2B shows another view of the illustrative prior-art method shown in FIG. 2A.

FIG. 2B shows a position of outer sheath 205 of catheter 201 inserted into nasal cavity 123*a* of anatomically correct model 202. Markings on outer sheath 205 show outer sheath 205 has been inserted approximately 6 cm into nasal cavity 123*a* and then retracted about 1 cm to expose distal tip 207. FIG. 2B shows that outer sheath 205 is positioned anteriorly relative to inferior turbinate 107*a*, anterior to middle turbinate 109*a* and superior turbinate 111*a*. Even after approximately 6 cm of insertion into nasal cavity 123*a*, distal tip 207 is still relatively far from an estimated position of SPG 115*a*.

Figure 2C:
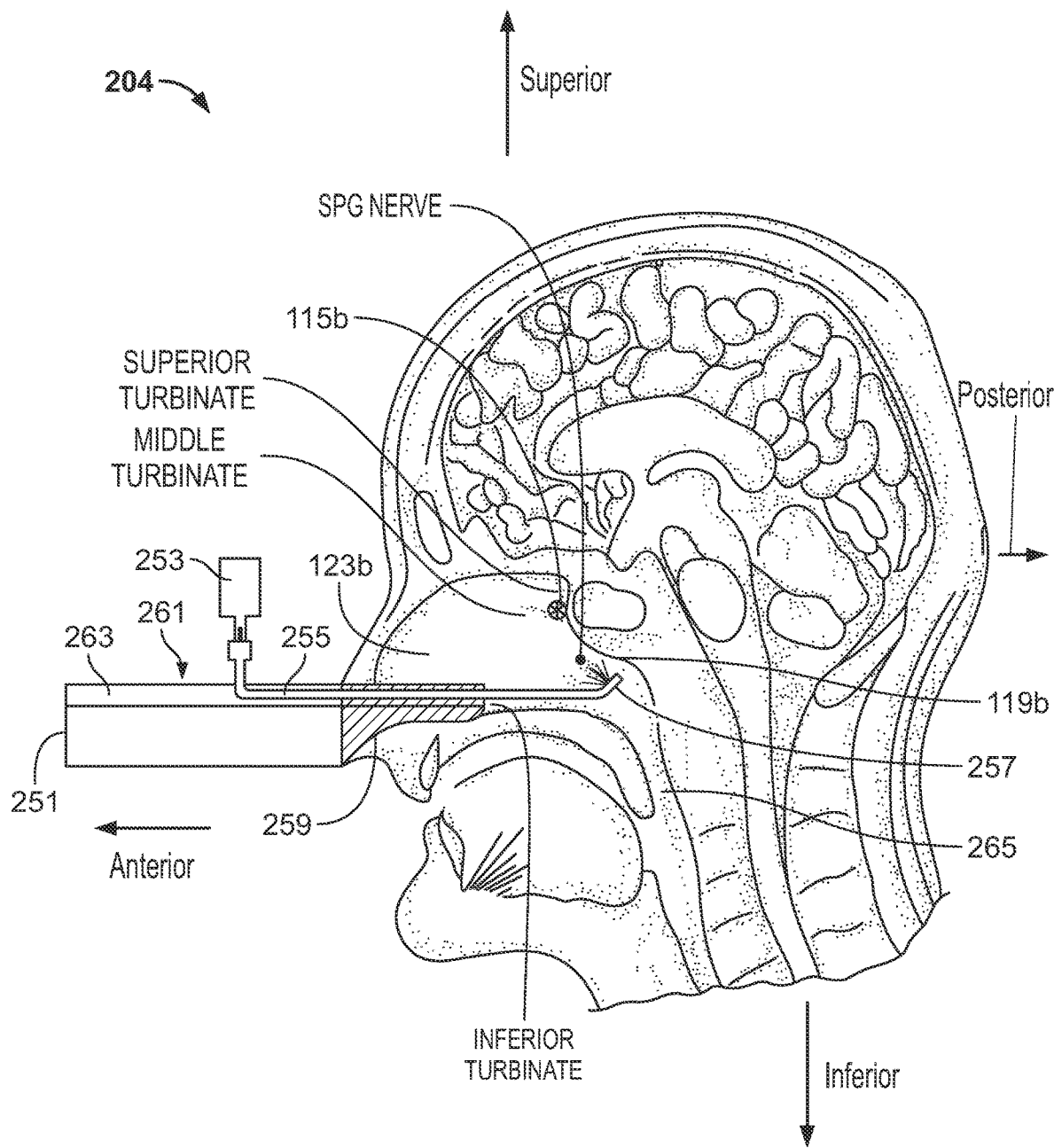
FIG. 2C shows an illustrative prior-art method of administering an SPG block.

FIG. 2C shows illustrative prior-art method 204 for administering a SPG blockade. Method 204 shown in FIG. 2C may be employed in connection with use of a Tx360® device and administered with a patient in a seated and upright position. The location of the "SPG nerve" in FIG. 2C is shown in accordance with the disclosure of U.S. Pat. Nos. 8,231,588 and 8,905,980 associated with the Tx360® device.

Introducer 261 includes passageway 263. Catheter 257 is slidable in passageway 263. Introducer 261 includes proximal end 251 that remains outside a nostril of the patient. Introducer 261 includes distal tip 259 that is inserted into the nostril. Method 204 includes positioning distal tip 259 of introducer 261 in the nostril. Method 204 include moving catheter 257 through passageway 263 in a posterior direction, and out of distal tip 259. When fully extended from distal tip 259, distal tip 257 of catheter 257 may extend into a region of nasal cavity 123*b* that is posterior and inferior to the "SPG nerve." After extending distal tip 257, medicament 253 may be released from distal tip 257 toward the "SPG nerve." Method 204 includes releasing a dosage of medicament 253 that ranges from about 0.1 cc to about 1.0 cc.

Methods 204 shown in FIG. 2C have not achieved desired efficacy results. As shown in FIG. 2C, medicament 253 is released when distal tip 257 is in a posterior/inferior to the "SPG nerve." After releasing medicament 253 from distal tip 257, gravity pulls medicament 253 into oropharynx 265 instead of reaching the "SPG nerve."

Furthermore, a more accurate anatomical location of the SPG is at location 115*b*. Location 115*b* is aligned with a superior meatus, between posterior ends of superior and middle turbinates. As shown in in FIG. 2C, method 204 positions distal tip 257 too far from SPG location 115*b* for medicament 253 to have a desired therapeutic effect for treating headaches. Method 204 may therefore have the "spray and pray" deficiencies associated with method 200 (shown above in FIG. 2A). Additionally, when distal tip 257 is positioned in nasal cavity 123*b* as shown in FIG. 2C, sphenoid bone 119*b* may obstruct medicament 253 released from distal tip 257 from reaching SPG location 115*b*.

Figure 3A:
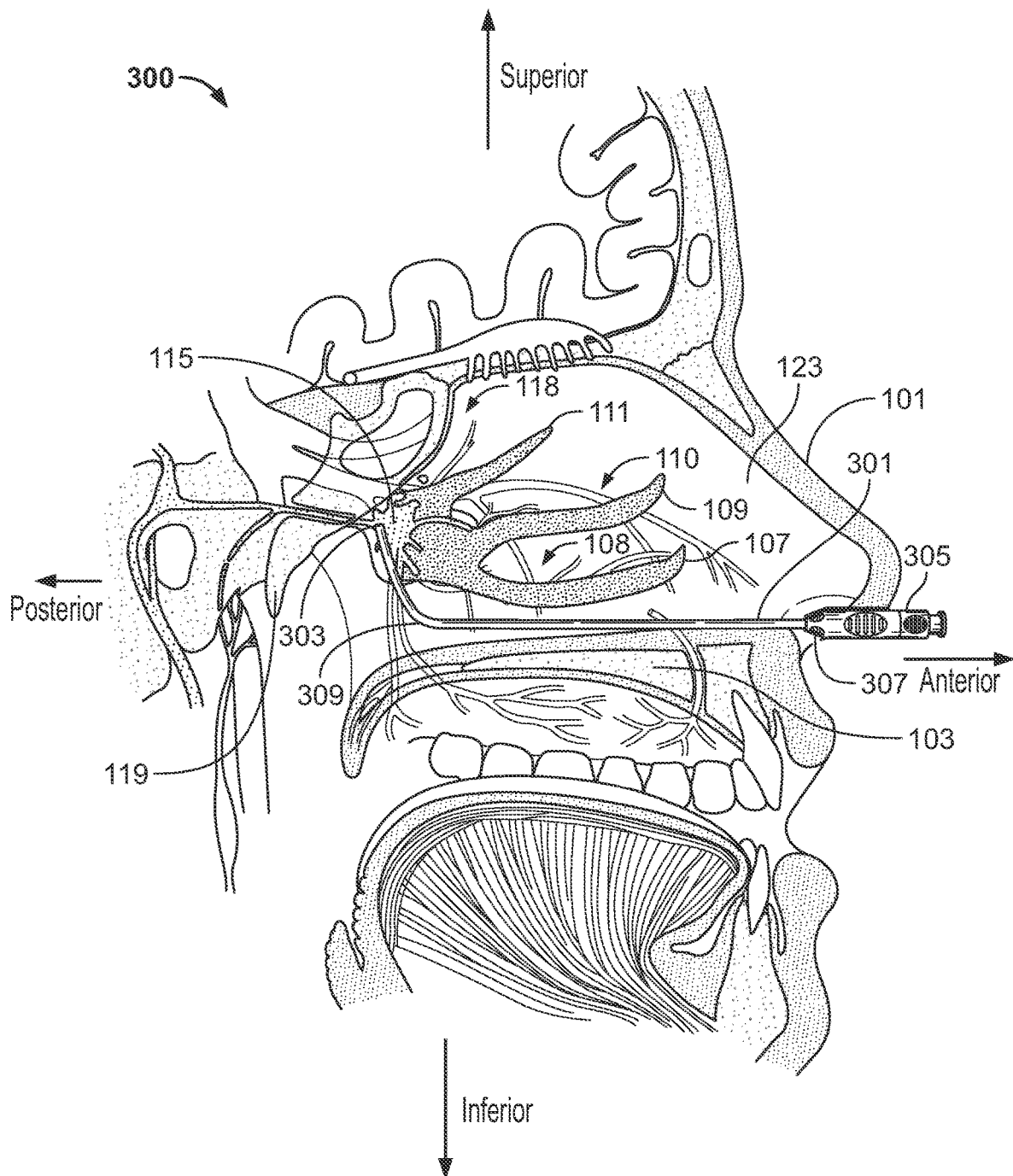
FIG. 3A shows an illustrative method of administering an SPG block in accordance with principles of the disclosure.

FIG. 3A shows method 300 in accordance with principles of this disclosure. Method 300 includes inserting catheter 301 into nostril 105 (shown in FIG. 1). Catheter 301 may be inserted into nostril 105 until hub 307 of handle 305 contacts nostril 105. Catheter 301 may be advanced parallel to a superior surface of hard palate 103. Catheter 301 may be advanced through inferior meatus 106 (shown in FIG. 1). Catheter 301 may be advanced until distal tip 303 of catheter 301 contacts a posterior wall of nasal cavity 123.

After contacting the posterior wall of nasal cavity 123, continuing to advance catheter 301 into nostril 105 and through inferior meatus 106 may cause catheter 301 to develop bend 309. Catheter 301 may be sufficiently flexible to allow bend 309 to form when advancing catheter 301 through inferior meatus 106. Catheter 301 may also be sufficiently rigid so that after catheter 301 develops bend 309, continuing to advance catheter 301 into nostril 105 causes distal tip 303 to advance superiorly to inferior turbinate 107.

Catheter 301 may be the outer sheath of a SphenoCath® catheter, part number DT1001GP-3, provided by Dolor Technologies LLC, Clearfield, Utah. The aforementioned SphenoCath® includes an inner catheter within an outer sheath. Devices used in accordance with method 300 may not include the inner catheter. Devices used in accordance with method 300 may include a single lumen device. The single lumen device may have properties (e.g., hardness, length and/or diameter) of the outer sheath of the SphenoCath®. The single lumen device may have flexibility properties of the outer sheath of the SphenoCath® when the inner catheter is retracted inside the outer sheath. A presence of the inner catheter within the outer sheath may increase rigidity of the outer sheath.

At a posterior/inferior corner of the nasal cavity, the torus tubarius (not shown) extends from a lateral wall of nasal cavity 123 and surrounds a pharyngeal opening to the auditory tube. Salpingopharyngeal folds (not shown) descends inferiorly from the torus tubarius between the pharyngeal recess (not shown) and soft palate (not shown). Advancing catheter 301 into nostril 105 may bring distal tip 303 into contact the torus tubarius and/or salpingopharyngeal folds. Contact with the torus tubarius and/or salpingopharyngeal folds may direct distal tip 303 superiorly, creating bend 309.

Catheter 301 may be advanced into nostril 105 until distal tip 303 is positioned between posterior ends of middle turbinate 109 and superior turbinate 111. Catheter 301 may be advanced into nostril 105 until distal tip 303 is in a position superior to a posterior end of middle turbinate 109.

In some embodiments (not shown in FIG. 3A), catheter 301 may be advanced into nostril 105 until distal tip 303 is in sphenoethmoid recess 118. Catheter 301 may be advanced into nostril 105 until distal tip 303 is within 4 mm of SPG 115. Catheter 301 may be advanced into nostril 105 until distal tip 303 contacts mucosa of SPG 115. Mucosa of SPG 115 may be posterior and superior to a posterior end of middle turbinate 109.

In a preferred embodiment, distal tip 303 is advanced at least 8 cm into nostril 105. After distal tip 303 of catheter 301 is advanced at least 8 cm into nostril 105, medicament may be released from distal tip 303. The medicament may be 3 cc of 2% lidocaine. The released 3 cc of medicament may bathe the SPG. Because distal tip 303 is at SPG 115, or at least within 4 mm of SPG 115, the released medicant may have a greater therapeutic efficacy than prior-art methods of blockading SPG 115. Method 300 may be performed on both right and left nostrils of a human patient. 3 cc of medicament may be released in each nostril.

Figure 3B:
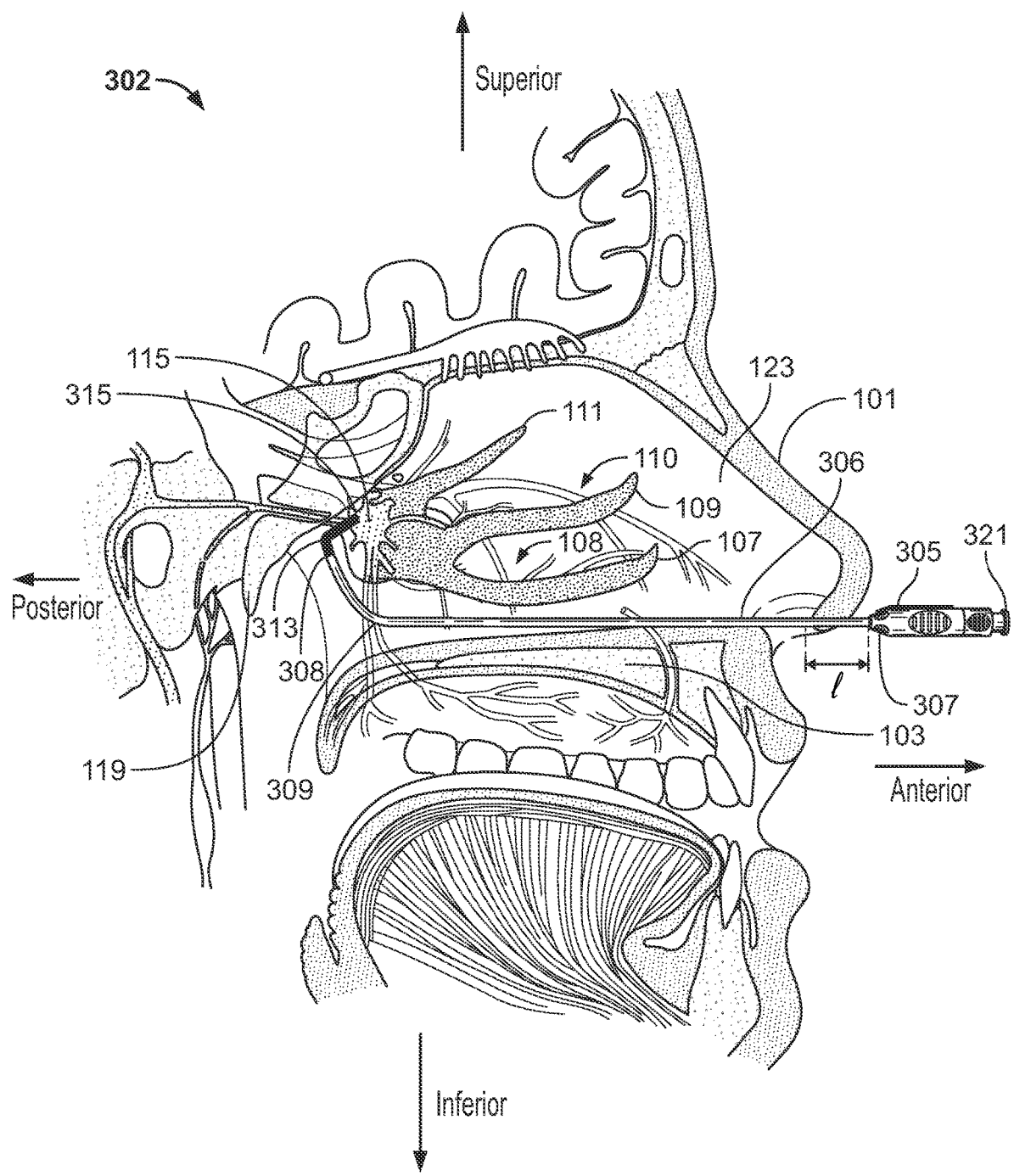
FIG. 3B shows an illustrative method of administering an SPG block in accordance with principles of the disclosure.

FIG. 3B shows illustrative method 302. Method 302 may include one or more steps of method 300 shown in FIG. 3A. In method 302, outer sheath 306 has been inserted into nostril 105. Outer sheath 306 may have been inserted into nostril 105 until distal tip 308 is positioned as distal tip 303 is shown in FIG. 3A. An inner catheter may be disposed within outer sheath 306. The inner catheter may be affixed to handle 321. Inner catheter may be slidable within outer sheath 306 my actuating handle 321. Handles 321 and 305 may be slidable with respect to each other.

FIG. 3B shows that outer sheath 306 has been retracted out (in an anterior direction) of nostril 105 by distance 1. An illustrative distance 1 may be 1 cm. Retracting outer sheath 306 may expose distal tip 315 of the inner catheter. The inner catheter may be biased to have an intrinsic curvature. The biasing may cause inner catheter to form bend 313 when outer sheath 306 is retracted out of nostril 105 by distance 1.

The biasing may allow a practitioner to manipulate handle 305 or 321 so that distal tip 315 of the inner catheter is positioned close (at least 4 mm) to a center of SPG 115. The biasing may allow a practitioner to manipulate handle 305 or 321 so that distal tip 315 of the inner catheter is positioned in contact with SPG 115. The biasing of the inner catheter may provide a practitioner the ability to move distal tip 315 medially or laterally within nasal cavity 123. The ability to move distal tip 315 medially or laterally within nasal cavity 123 may allow distal tip 315 to be positioned closer to SPG 115 before releasing medicament from distal tip 315.

Method 302 may include releasing medicament from distal tip 315. The medicament may be 3 cc of 2% lidocaine. The releasing of 3 cc of medicament may bathe SPG 115. Because distal tip 315 is at SPG 115, or at least within 4 mm of SPG 115, the released medicant may have a greater therapeutic efficacy than prior-art methods of blockading SPG 115. Method 302 may be performed on both right and left nostrils of a human patient. 3 cc of medicament may be released in each nostril.

Figure 3C:
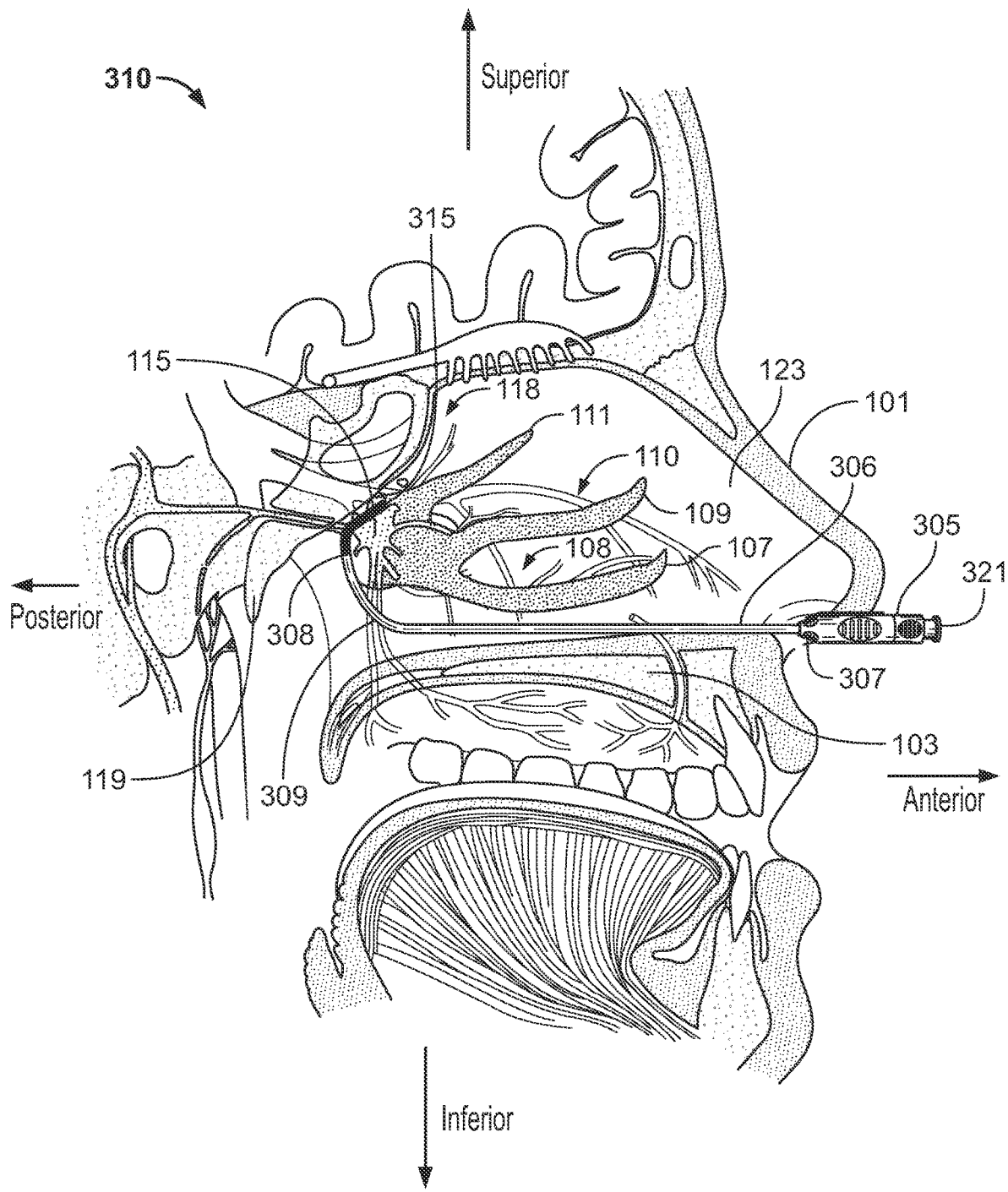
FIG. 3C shows an illustrative method of administering an SPG block in accordance with principles of the disclosure.

FIG. 3C shows illustrative method 310. Method 310 may include one or more steps of method 300 shown in FIG. 3A. Method 310 may include one or more steps of method 302 shown in FIG. 3B. In method 310, outer sheath 306 has been inserted into nostril 105. Outer sheath 306 may have been inserted into nostril 105 until distal tip 308 is positioned as distal tip 303 is shown in FIG. 3A. Distal tip 308 may be inserted at least 8 cm into nostril 105.

Figure 7:
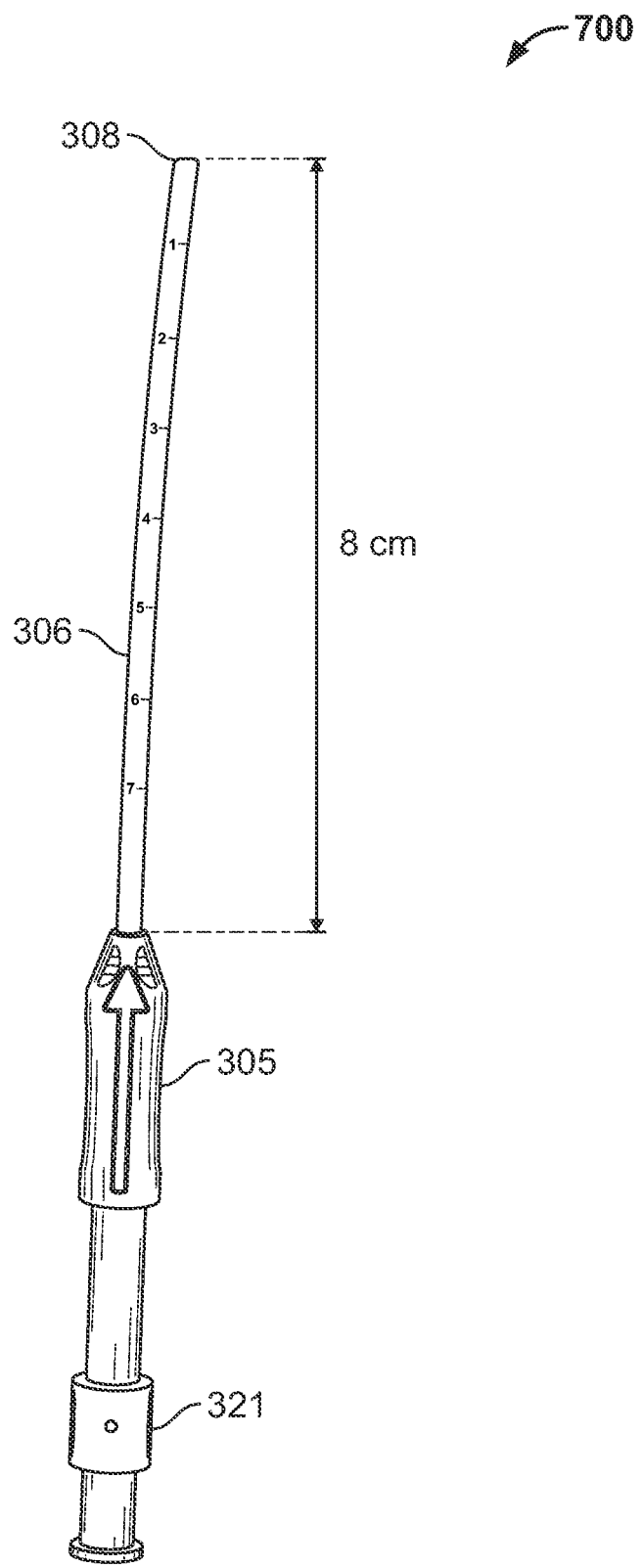
FIG. 7 shows an illustrative apparatus for administering an SPG block in accordance with principles of the disclosure.

An inner catheter may be disposed within outer sheath 306. The inner catheter may be affixed to handle 321. Inner catheter may be slidable within outer sheath 306 my actuating handle 321. Handles 321 and 305 may be slidable with respect to each other. Outer sheath 306 may be inserted into nostril 105 when inner catheter is retracted within outer sheath 306. FIG. 7 shows inner catheter retracted within outer sheath 306. Distal tip 308 may be inserted into nostril 105 until hub 307 contacts nostril 105. Distal tip 308 may be inserted at least 8 cm into nostril 105.

Figure 6:
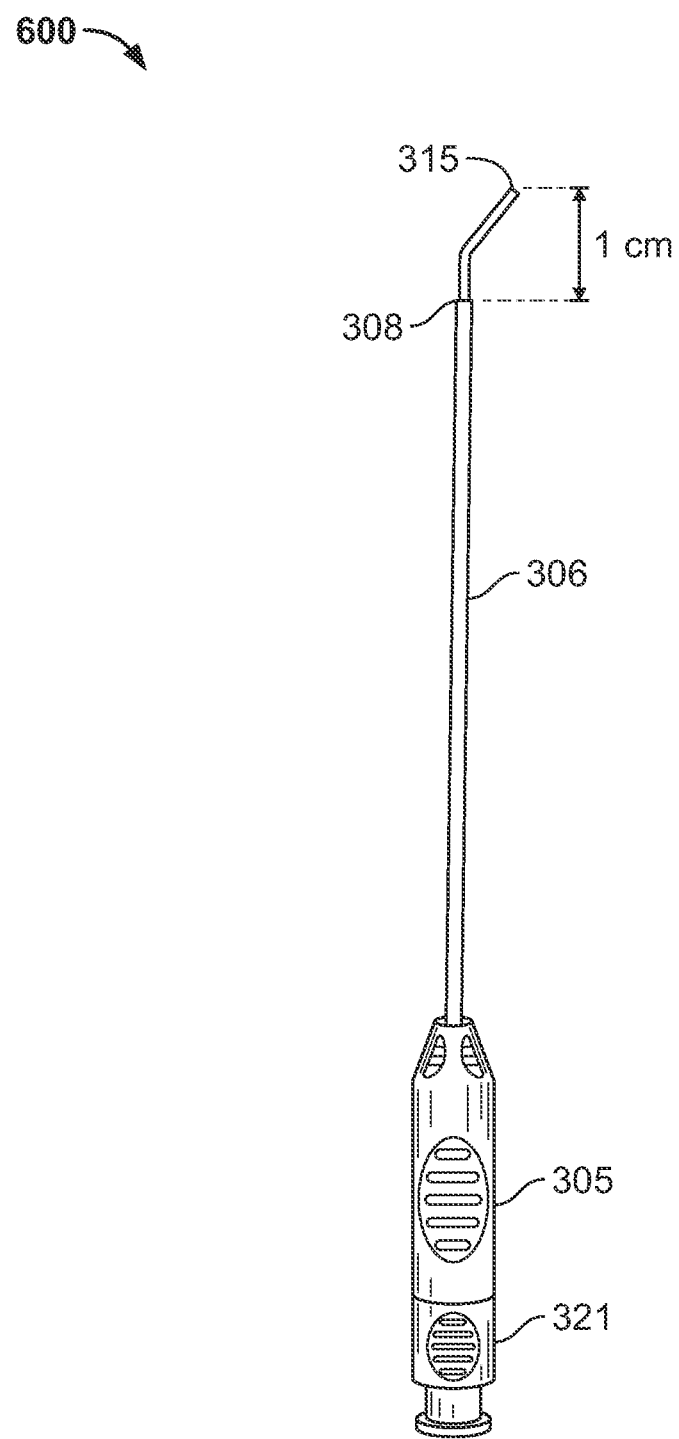
FIG. 6 shows an illustrative apparatus for administering an SPG block in accordance with principles of the disclosure.

FIG. 3C shows that distal tip 315 of the inner catheter has been pushed out of outer sheath 306. FIG. 6 shows distal tip 315 pushed out of outer sheath 306. Distal tip 315 may be pushed out of outer sheath 306 by pushing handle 321 in a posterior direction after hub 307 is seated against nostril 105. As shown in FIGS. 6 and 7, distal tip 315 may be configured to extend at least 1 cm beyond distal tip 308.

Pushing distal tip 315 out of outer sheath 306 may position distal tip 315 posterior to turbinates 111, 109 and 107. Pushing distal tip 315 out of outer sheath 306 may position distal tip 315 superior to SPG 115. Pushing distal tip 315 out of outer sheath 306 may extend a distance traveled by distal tip 315 from nostril 105 to at least 9 cm. Advancing distal tip 315 at least 9 cm from nostril 105 in the manner shown in FIG. 3C may position distal tip within 4 mm of SPG 115. Advancing distal tip 315 at least 9 cm from nostril 105 in the manner shown in FIG. 3C may position distal tip in contact with SPG 115.

The inner catheter may be biased to have an intrinsic curvature. The biasing may cause inner catheter to bend when extended beyond distal tip 308. The biasing may allow a practitioner to manipulate handle 321 so that distal tip 315 of the inner catheter is positioned close (at least 4 mm) to a center of SPG 115. The biasing may allow a practitioner to manipulate handle 321 so that distal tip 315 of the inner catheter is positioned in contact with SPG 115. The biasing of the inner catheter may provide a practitioner the ability to move distal tip 315 medially or laterally within nasal cavity 123. The ability to move distal tip 315 medially or laterally within nasal cavity 123 may allow distal tip 315 to be positioned closer to SPG 115 before releasing medicament from distal tip 315.

Method 310 may include releasing medicament from distal tip 315. The medicament may be 3 cc of 2% lidocaine. The releasing of 3 cc of medicament may bathe SPG 115. Because distal tip 315 is at SPG 115, or at least within 4 mm of SPG 115, the released medicant may have a greater therapeutic efficacy than prior-art methods of blockading SPG 115. Method 310 may be performed on both right and left nostrils of a human patient. 3 cc of medicament may be released in each nostril.

Figure 3D:
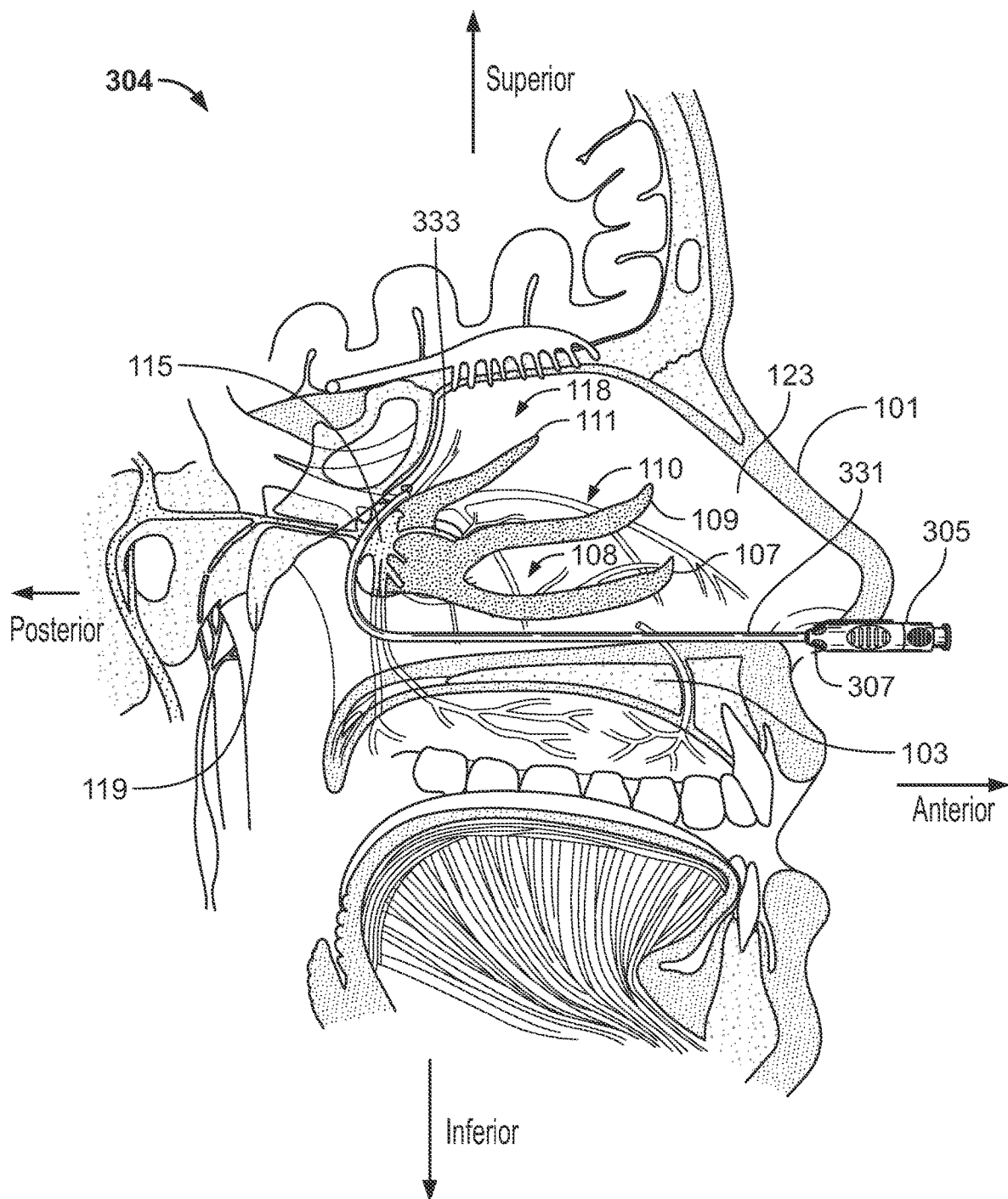
FIG. 3D shows an illustrative method of administering an SPG block in accordance with principles of the disclosure.

FIG. 3D shows illustrative method 304. Method 304 may include one or more steps of method 300 shown in FIG. 3A. Method 304 may include one or more steps of method 302 shown in FIG. 3B. Method 304 may include one or more steps of method 310 shown in FIG. 3C. Method 304 shows that catheter 331 has been inserted into nasal cavity 123 and advanced through inferior meatus 106 (shown in FIG. 1). Catheter 331 may be constructed of a material that is flexible and bends on contact with a posterior wall of nasal cavity 123. Catheter 331 may be constructed of a material that is flexible and bends when contacting a torus tubarius or other structures at or near a posterior wall of nasal cavity 123. Catheter 331 may be constructed of a material that is stiff enough to continue to advance superiorly after bending.

For example, catheter 331 may be constructed from semi-rigid rigid Tecothane®, an aromatic polyurethane available from Lubrizol Advanced Materials, Inc. of Cleveland, Ohio. An illustrative catheter 331 may be an outer sheath of a SphenoCath® catheter, part number DT1001GP-3, available from Dolor Technologies LLC, of Clearfield, Utah.

Method 304 shows that distal tip 333 of catheter 331 may be positioned superior to SPG 115. Method 304 shows that distal tip 333 of catheter 331 may be positioned in spheno-ethmoid recess 118. Method 304 may include releasing medicament from distal tip 333. Medicament released from distal tip 333 may be 3 cc of 2% lidocaine.

The releasing of 3 cc of medicament may bathe SPG 115. Because distal tip 3331 is superior to SPG 115 and posterior to turbinates 107, 109 and 111, the released medicant may have a greater therapeutic efficacy than prior-art methods of blockading SPG 115. Method 304 may be performed on both right and left nostrils of a human patient.

In some embodiments, method 304 may include releasing medicament directly from distal tip 333. In some embodiments, an inner catheter may be positioned within catheter 331. In such embodiments, method steps may include retracting catheter 331 to expose a distal tip of the inner catheter. The distal tip of the inner catheter may be biased to have a pre-defined curvature. Methods may include adjusting an orientation of the inner catheter.

For example, a distal tip of the inner catheter may be adjusted to point in a medial or lateral direction. Adjusting an orientation of the inner catheter may position a distal tip of the inner catheter closer to SPG 115. Methods may include releasing medicament from a distal tip of the inner catheter. Because method 304 includes releasing medicament from a position that is superior to SPG 115 and posterior to turbinates 107, 109 and 111, method 115 may have a greater therapeutic efficacy than prior-art methods of blockading SPG 115.

Figure 4:
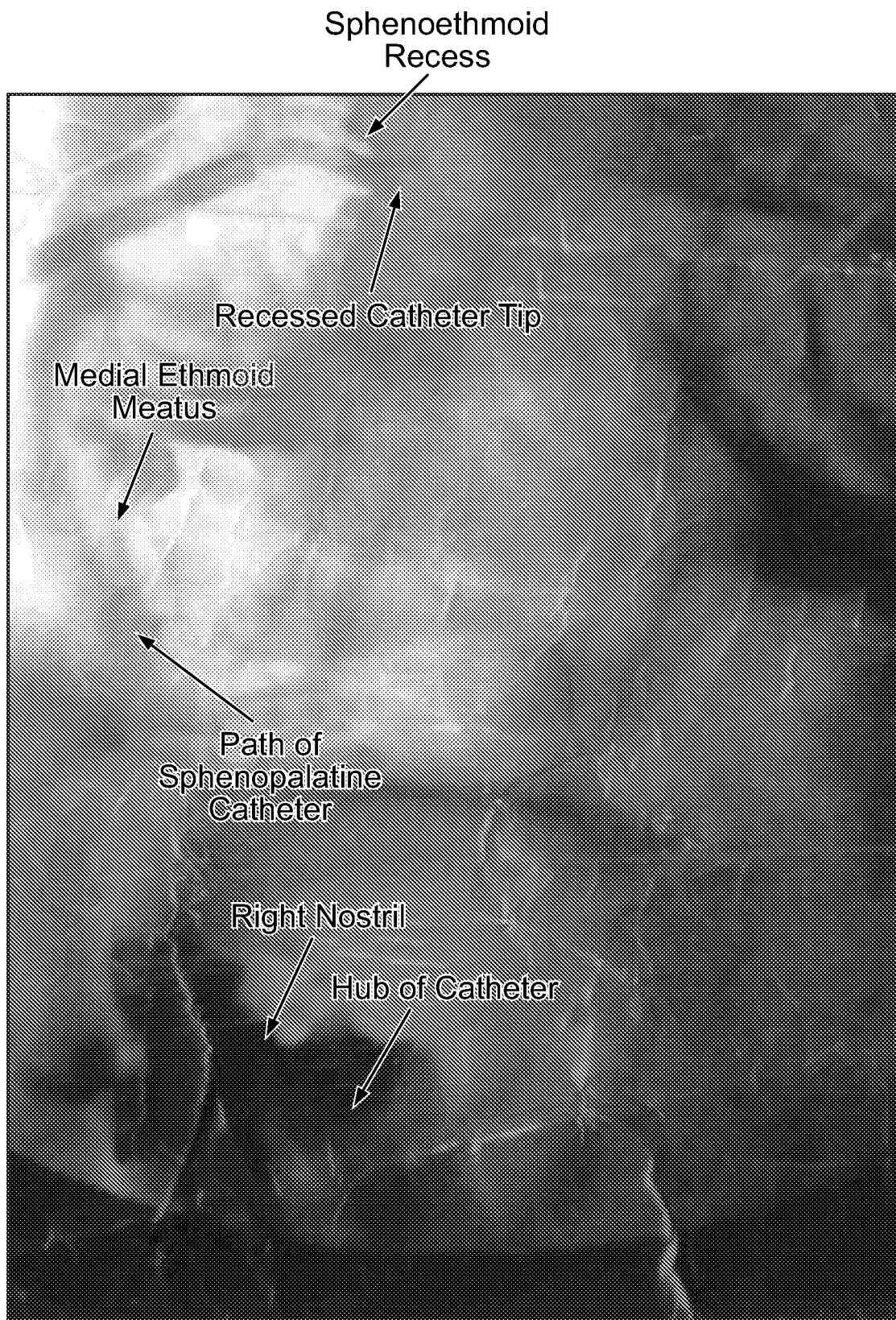
FIG. 4 shows an illustrative fluoroscopic image of a catheter inserted into a nasal cavity in accordance with principles of the disclosure.

FIG. 4 shows a fluoroscopic image of a distal tip of a catheter positioned in the nasal cavity using the methods described herein. This figure shows the catheter tip adjacent the sphenoethmoid recess.

Figure 5:
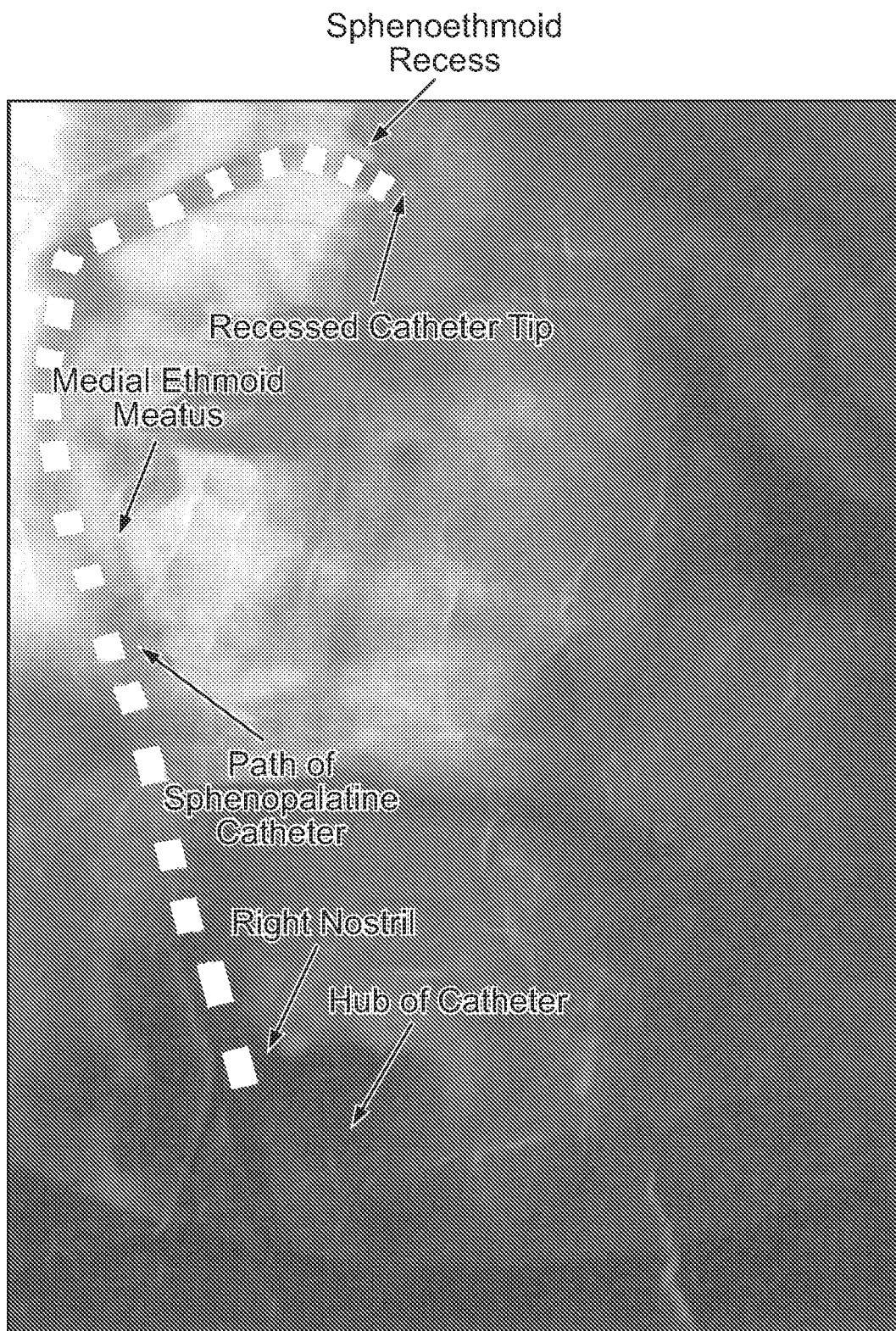
FIG. 5 shows an annotated image of FIG. 4 showing a path of the catheter inserted into the nasal cavity in accordance with principles of the disclosure.

FIG. 5 is an annotated fluoroscopic image of FIG. 4. FIG. 5 shows in broken white line, the path of the distal tip from a nostril to a position of the distal tip in the nasal cavity shown in FIG. 4. FIG. 5 shows that the catheter bends twice to reach the shown position of the distal tip.

FIG. 6 shows view 600 of an illustrative device that may be used in connection with the methods disclosed herein. View 600 shows outer sheath 306 (shown in FIG. 3B) in a retracted position exposing position a distal tip 315 of an inner catheter disposed within outer sheath 306.

FIG. 7 shows view 700 of the device shown in FIG. 6 and FIG. 3A with outer sheath 306 fully extended over the distal tip 315 of the inner catheter. View 700 also shows that outer sheath 306 has an illustrative length of 8 cm. Other embodiments may include catheters or outer sheaths that have lengths of more than 8 cm. For example, catheters used in connection with methods disclosed herein may be 9 cm, 10 cm, 11 cm, 12 cm, 13 cm or longer.

Figure 8:
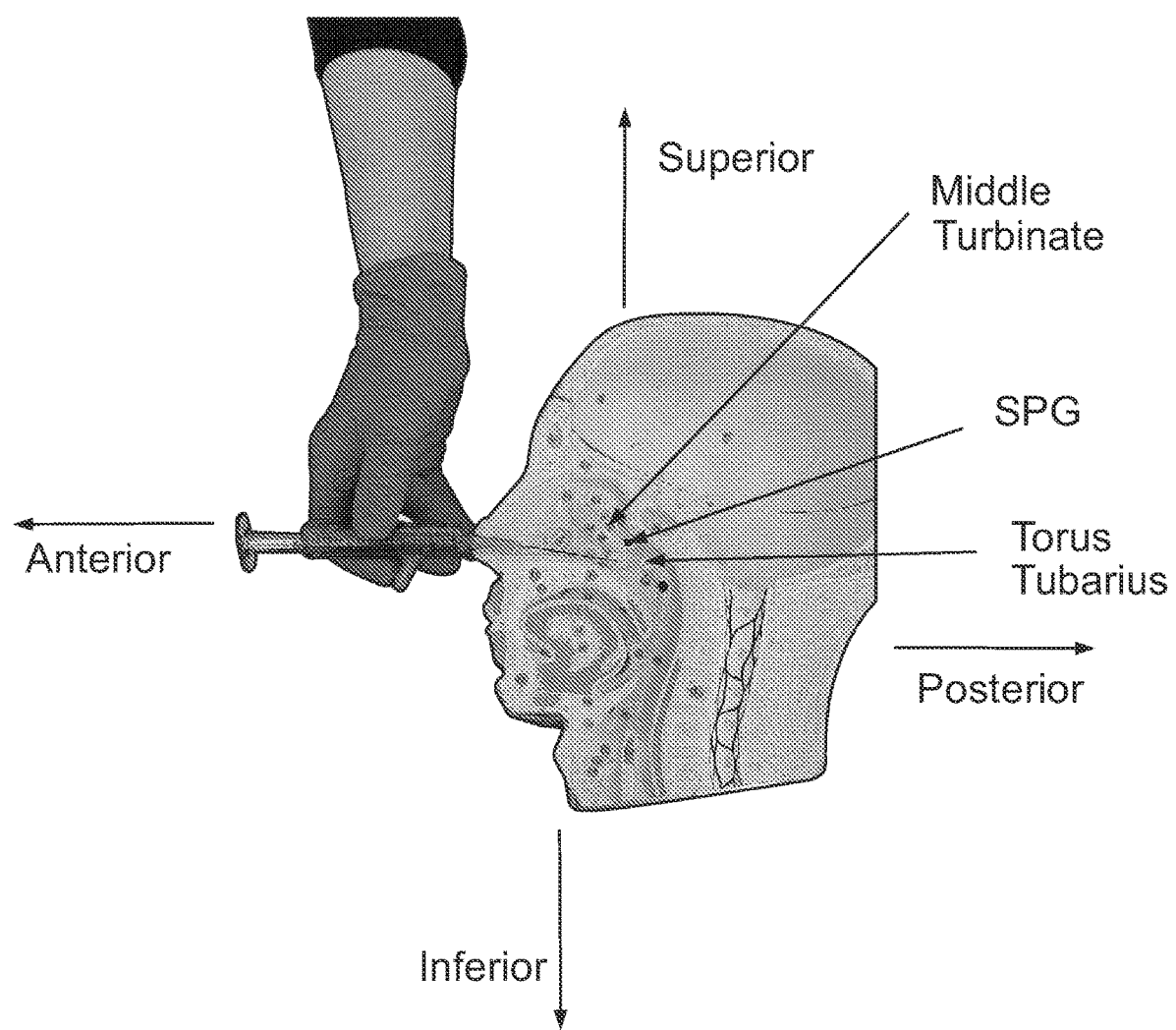
FIG. 8 shows a prior-art method and apparatus in connection with an anatomically correct model.

FIG. 8 shows a Tx360® device implementing prior-art methods (described in connection with FIG. 2C) on an anatomically correct model. The anatomically correct model shown in FIG. 8 is used by the anatomy department at a well-known medical school. FIG. 8 shows that a distal tip of the Tx360® will not reach the SPG. FIG. 8 shows that a distal tip of the Tx360® will be positioned inferior to the middle turbinate. FIG. 8 shows that a distal tip of the Tx360® will be positioned anterior to a posterior end of the middle turbinate. FIG. 8 shows that methods used in connection with a Tx360® device will not be as effective as methods disclosed herein to administer an SPG blockade.

Figure 9A:
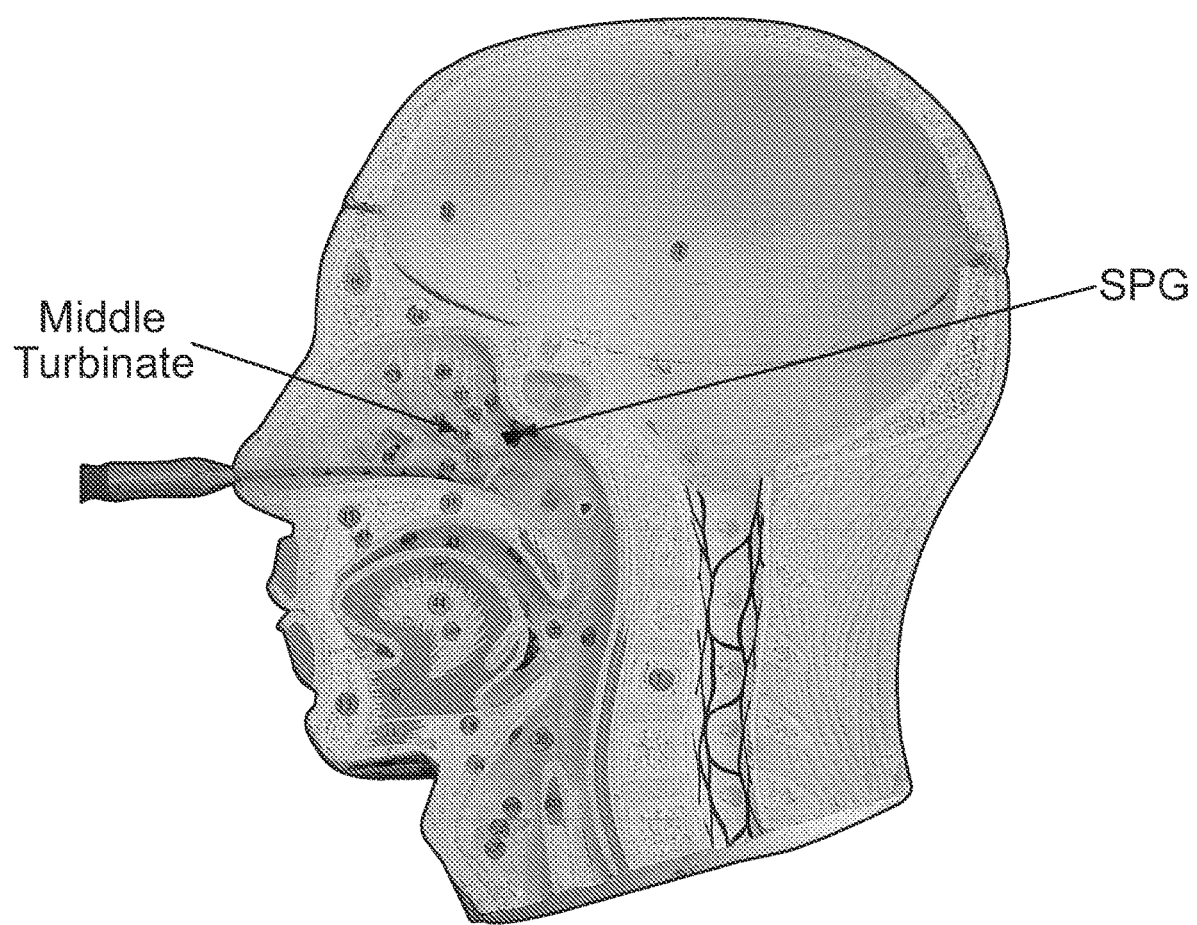
FIG. 9A shows an illustrative method and apparatus connection with an anatomically correct model and in accordance with principles of the disclosure.

FIG. 9A shows an illustrative view of a catheter inserted into a nasal cavity in accordance with method 310 disclosed in connection with FIG. 3C and on the same anatomically correct model shown in FIG. 8. FIG. 9A shows a catheter inserted into a nasal cavity in accordance with methods 310 that position a distal tip of the catheter posterior to a middle turbinate. FIG. 9A shows an illustrative view of distal tip of the inner catheter (e.g., 315 shown in FIG. 3C) positioned closer to the SPG than prior-art methods shown in FIG. 8.

Figure 9B:
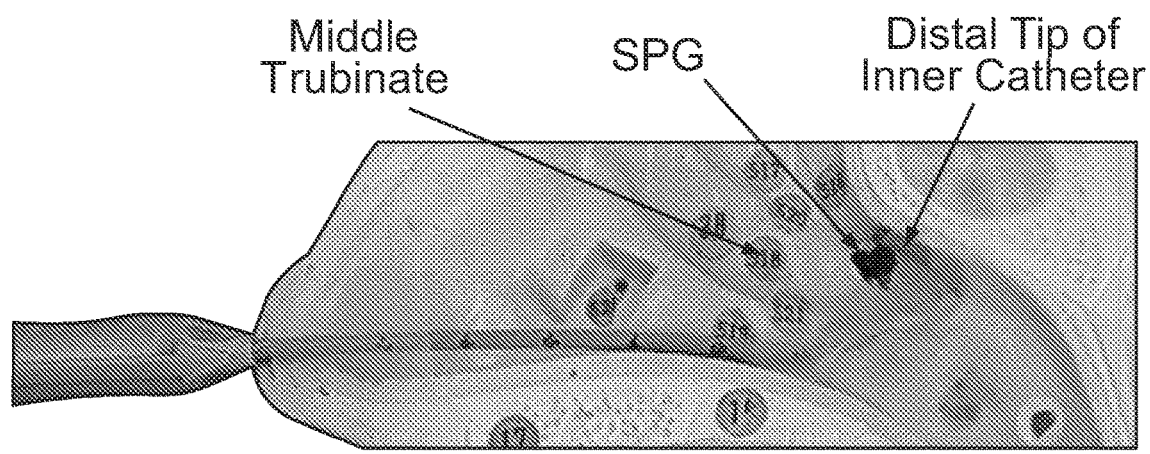
FIG. 9B shows a close-up and partial view of the illustrative method and apparatus shown in FIG. 9A.

FIG. 9B shows a close-up view of the position of distal tip (e.g., 315 shown in FIG. 3C) shown in FIG. 9A. FIG. 9B shows a close-up view of the position of the distal tip of the inner catheter relative to the middle turbinate and SPG. FIG. 9B shows that the distal tip has been inserted 9-10 cm past the nostril.

Figure 9C:
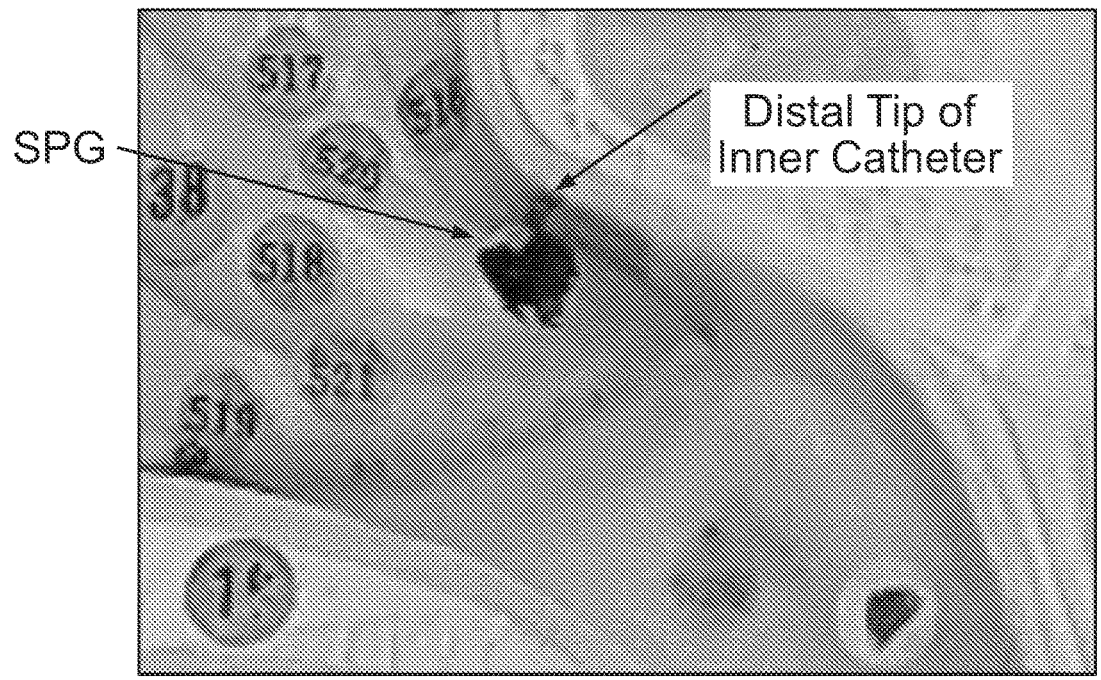
FIG. 9C shows a close-up and partial view of the illustrative method and apparatus shown in FIG. 9A.
Figure 9D:
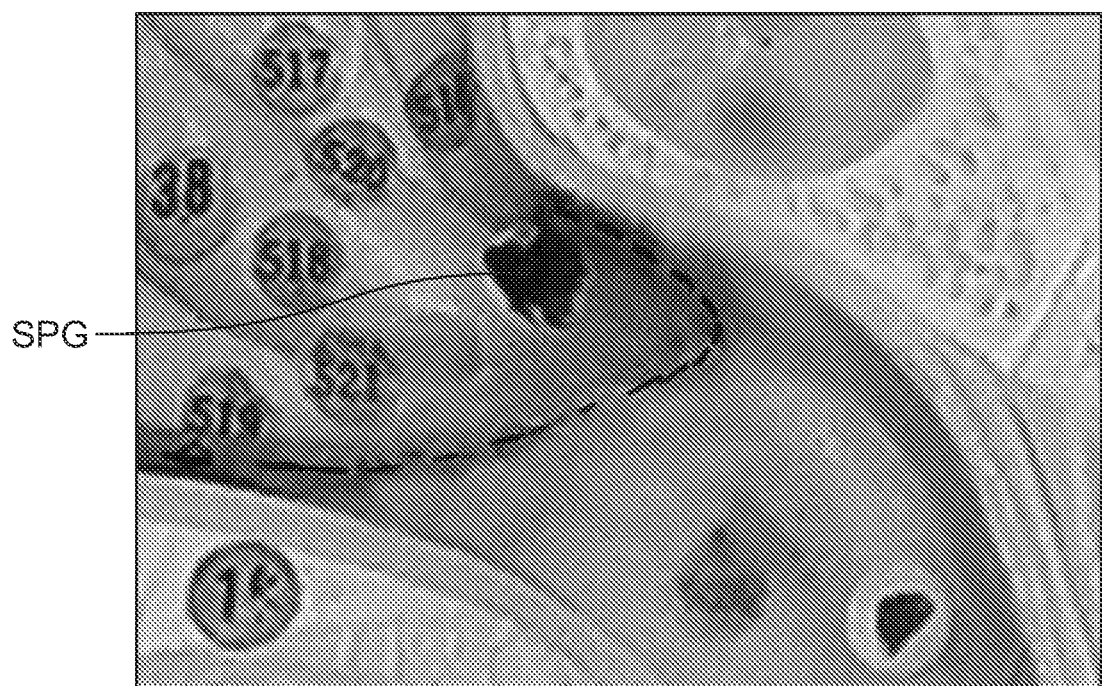
FIG. 9D shows an annotated image of FIG. 9C showing a path of the catheter inserted into the nasal cavity in accordance with principles of the disclosure.

FIG. 9C shows another close-up and partial view of the position of the distal tip of the inner catheter shown in FIG. 9A. FIG. 9C shows that using the innovative apparatus and methods disclosed herein, distal tip of the catheter (e.g., 315 shown in FIG. 3C) is in contact with a posterior/superior portion of the SPG. FIG. 9D shows an annotated image of FIG. 9C showing a path of the catheter inserted into the nasal cavity in accordance with principles of the disclosure.

Methods may in include releasing a medicament from the distal tip of the inner catheter when positioned in the nasal cavity as shown in in FIGS. 9A, 9B, 9C and 9D. Medicament released from distal tip of the inner catheter may be 3 cc of 2% lidocaine or any other suitable medicament for effecting a blockade of the SPG. Because methods and apparatus for blockading the SPG shown in FIGS. 9A, 9B, 9C and 9D include releasing medicament from a distal tip of the inner catheter that is positioned closer to SPG than prior-art methods, methods and apparatus shown in FIGS. 9A, 9B, 9C and 9D may have a greater therapeutic efficacy than prior-art methods of blockading the SPG.

Figure 10:
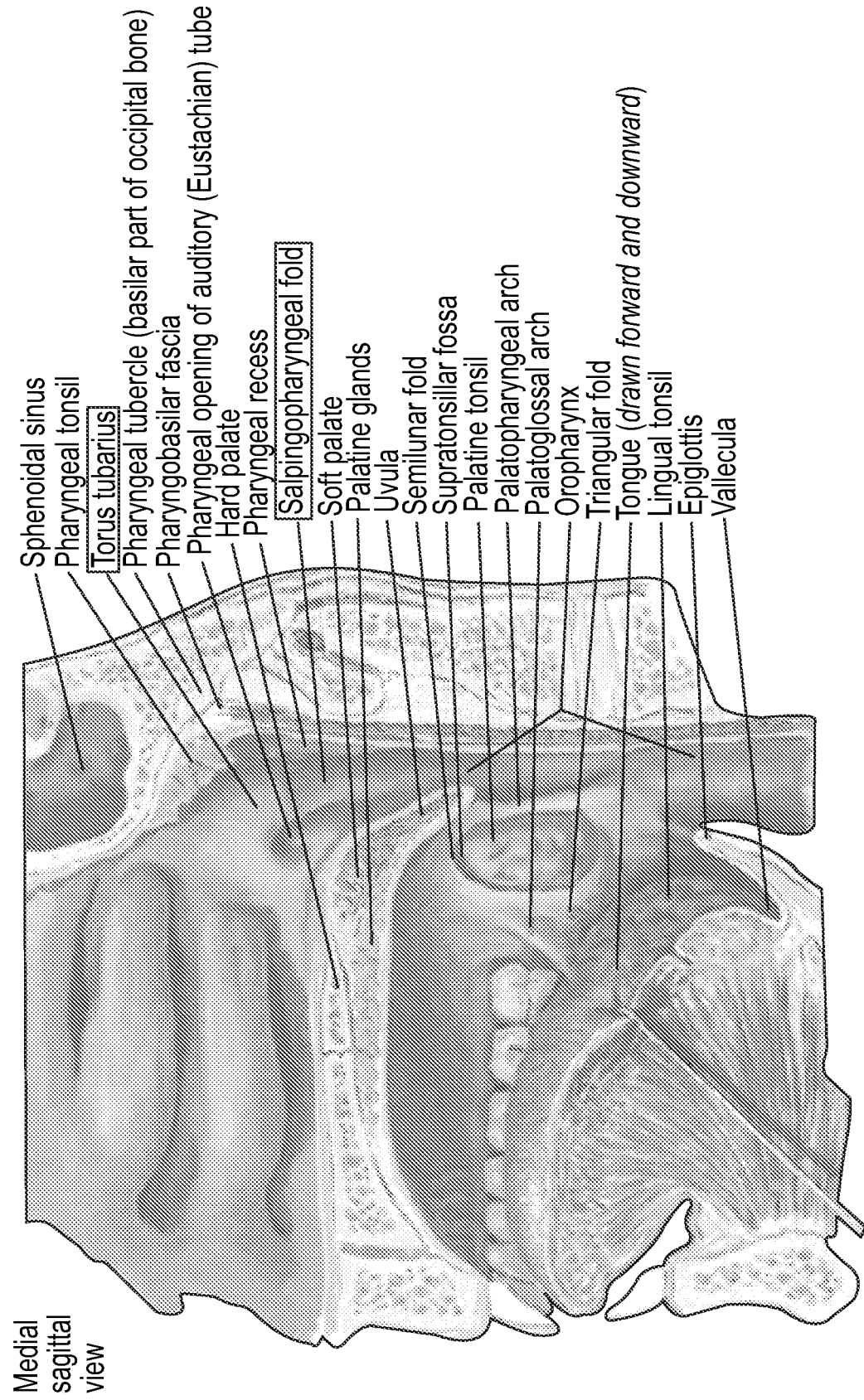
FIG. 10 shows illustrative anatomy near a posterior nasal cavity wall.

FIG. 10 shows illustrative anatomy near a posterior nasal cavity wall. FIG. 10 shows torus tubarius and salpingopharyngeal fold and other anatomy.

Thus, methods and apparatus for DEEP NASAL INSERTION SPHENOPALATINE GANGLION ("SPG") TREATMENT are provided. Persons skilled in the art will appreciate that the present disclosure can be practiced by other than the described embodiments, which are presented for purposes of illustration rather than of limitation, and that the present disclosure is limited only by the claims that follow.

I claim:

1. A catheter for delivering medicament to a sphenopalatine ganglion ("SPG"), the catheter comprising:
   a tube;
   a distal tip proximate to an end of the tube;
   means for introducing the medicament into the tube;
   the tube being advanceable into a nostril of a patient;
   the distal tip being positionable posterior and superior to a posterior middle turbinate of the patient;
   the tube being deflectable consistently in a superior direction near the distal tip by pushing the distal tip against a posterior wall of a nasal cavity of the patient; and
   means for releasing the medicament from the distal tip to the SPG.

2. The catheter of claim 1 further comprising means for the distal tip to contact the SPG.

3. The catheter of claim 1 wherein the tube is curved to match a surface of the nasal cavity.

4. A catheter for interacting with a sphenopalatine ganglion ("SPG"), the catheter comprising:
   a tube;
   a distal tip proximate to an end of the tube;

the tube being advanceable into a nostril of a patient;
the distal tip being positionable posterior and superior to a posterior middle turbinate of the patient;
the tube being deflectable consistently in a superior direction near the distal tip by pushing the distal tip against a posterior wall of a nasal cavity of the patient; and
means for interacting with the SPG proximate to the distal tip.

5. The catheter of claim 4 wherein the means for interacting is electrical stimulation.

6. The catheter of claim 4 wherein the means for interacting is a laser.

7. The catheter of claim 4 wherein the means for interacting is ultrasound.

8. The catheter of claim 4 wherein the means for interacting is a camera.

* * * * *